United States Patent
Donoho et al.

(10) Patent No.: US 6,716,614 B1
(45) Date of Patent: Apr. 6, 2004

(54) HUMAN CALCIUM DEPENDENT PROTEASES, POLYNUCLEOTIDES ENCODING THE SAME, AND USES THEREOF

(75) Inventors: Gregory Donoho, Portage, MI (US); C. Alexander Turner, Jr., The Woodlands, TX (US); Michael C. Nehls, Stockdorf (DE); Glenn Friedrich, Houston, TX (US); Brian Zambrowicz, The Woodlands, TX (US); Arthur T. Sands, The Woodlands, TX (US)

(73) Assignee: Lexicon Genetics Incorporated, Woodlands, TX (US)

( * ) Notice: Subject to any disclaimer, the term of this patent is extended or adjusted under 35 U.S.C. 154(b) by 0 days.

(21) Appl. No.: 10/202,619

(22) Filed: Jul. 23, 2002

Related U.S. Application Data

(63) Continuation-in-part of application No. 09/653,839, filed on Sep. 1, 2000, now Pat. No. 6,433,153.
(60) Provisional application No. 60/152,057, filed on Sep. 2, 1999.

(51) Int. Cl.[7] .............................. C12N 9/50; C12N 1/20; C12N 15/00; C07H 21/04
(52) U.S. Cl. ................... 435/219; 536/23.2; 435/252.3; 435/320.1
(58) Field of Search .............................. 435/219, 320.1, 435/252.3; 536/23.2

(56) References Cited

U.S. PATENT DOCUMENTS

| | | | |
|---|---|---|---|
| 4,190,496 A | 2/1980 | Rubenstein et al. |
| 4,215,051 A | 7/1980 | Schroeder et al. |
| 4,376,110 A | 3/1983 | David et al. |
| 4,594,595 A | 6/1986 | Struckman |
| 4,631,211 A | 12/1986 | Houghten |
| 4,683,195 A | 7/1987 | Mullis et al. |
| 4,683,202 A | 7/1987 | Mullis |
| 4,689,405 A | 8/1987 | Frank et al. |
| 4,713,326 A | 12/1987 | Dattagupta et al. |
| 4,800,159 A | 1/1989 | Mullis et al. |
| 4,873,191 A | 10/1989 | Wagner et al. |
| 4,946,778 A | 8/1990 | Ladner et al. |
| 5,075,217 A | 12/1991 | Weber |
| 5,252,743 A | 10/1993 | Barrett et al. |
| 5,272,057 A | 12/1993 | Smulson et al. |
| 5,283,173 A | 2/1994 | Fields et al. |
| 5,364,759 A | 11/1994 | Caskey et al. |
| 5,424,186 A | 6/1995 | Fodor et al. |
| 5,445,934 A | 8/1995 | Fodor et al. |
| 5,459,127 A | 10/1995 | Felgner et al. |
| 5,464,764 A | 11/1995 | Capecchi et al. |
| 5,468,614 A | 11/1995 | Fields et al. |
| 5,487,992 A | 1/1996 | Capecchi et al. |
| 5,491,084 A | 2/1996 | Chalfie et al. |
| 5,556,752 A | 9/1996 | Lockhart et al. |
| 5,625,048 A | 4/1997 | Tsien et al. |
| 5,627,059 A | 5/1997 | Capecchi et al. |
| 5,631,153 A | 5/1997 | Capecchi et al. |
| 5,667,973 A | 9/1997 | Fields et al. |
| 5,700,637 A | 12/1997 | Southern |
| 5,744,305 A | 4/1998 | Fodor et al. |
| 5,777,079 A | 7/1998 | Tsien et al. |
| 5,789,215 A | 8/1998 | Berns et al. |
| 5,795,737 A | 8/1998 | Seed et al. |
| 5,804,387 A | 9/1998 | Cormack et al. |
| 5,830,721 A | 11/1998 | Stemmer et al. |
| 5,837,458 A | 11/1998 | Minshull et al. |
| 5,874,304 A | 2/1999 | Zolotukhin et al. |
| 5,877,397 A | 3/1999 | Lonberg et al. |
| 5,948,767 A | 9/1999 | Scheule et al. |
| 5,968,750 A | 10/1999 | Zolotukhin et al. |
| 5,976,796 A | 11/1999 | Szalay et al. |
| 6,020,192 A | 2/2000 | Muzyczka et al. |
| 6,027,881 A | 2/2000 | Pavlakis et al. |
| 6,054,321 A | 4/2000 | Tsien et al. |
| 6,075,181 A | 6/2000 | Kucherlapati et al. |
| 6,087,555 A | 7/2000 | Dunstan et al. |
| 6,096,865 A | 8/2000 | Michaels |
| 6,110,490 A | 8/2000 | Thierry |
| 6,114,598 A | 9/2000 | Kucherlapati et al. |
| 6,136,566 A | 10/2000 | Sands et al. |
| 6,139,833 A | 10/2000 | Burgess et al. |
| 6,146,826 A | 11/2000 | Chalfie et al. |
| 6,150,584 A | 11/2000 | Kucherlapati et al. |
| 6,172,188 B1 | 1/2001 | Thastrup et al. |
| 6,207,371 B1 | 3/2001 | Zambrowicz et al. |
| 6,265,548 B1 | 7/2001 | Pavlakis et al. |

OTHER PUBLICATIONS

Askew et al, 1989, "Molecular Regulation with Convergent Functional Groups, 6. Synthetic and Structural Studies with a Model Receptor for Nucleic Acid Components", J. Am. Chem. Soc. 111:1082–1090.
Bird et al, 1988, "Single–Chain Antigen–Binding Proteins", Science 242:423–426.
Bitter et al, 1987, "Expression and Secretion Vectors for Yeast", Methods in Enzymology 153:516–544.
Brisson et al, 1984, "Expression of a Bacterial gene in plants by using a viral vector", Nature 310:511–514.
Broglie et al, 1984, "Light–Regulated Expression of a Pea Ribulose–1,5–Bisphosphate Carboxylase Small Subunit Gene in Transformed Plant Cells", Science 224:838–843.
Chein et al, 1991, "The two–hybrid system: A method to identify and clone genes for proteins that interact with a protein of interest", *Proc. Natl. Acad. Sci. USA* 88:9578–9582.
Colbere–Garapin et al, 1981, "A New Dominant Hybrid Selective Marker for Higher Eukaryotic Cells", J. Mol. Biol. 150:1–14.

(List continued on next page.)

*Primary Examiner*—P. Achutamurthy
*Assistant Examiner*—Yong Pak

(57) ABSTRACT

Novel human polynucleotide and polypeptide sequences are disclosed that can be used in therapeutic, diagnostic, and pharmacogenomic applications.

3 Claims, No Drawings

OTHER PUBLICATIONS

Coruzzi et al, 1984, "Tissue–specific and light–regulated expression of a pea nuclear gene encoding the small subunit of ribulose–1,5–bisphosphate carboxylase", EMBO Journal 3(8):1671–1679.

Cote et al., 1983, "Generation of human monoclonal antibodies reactive with cellular antigens," Proc. Natl. Acad. Sci. USA 80:2026–2030.

Gautier et al, 1987, "α–DNA IV:α–anomeric and β–anomeric tetrathymidylates covalently linked to intercalating oxazolopyridocarbazole. Synthesis, physiochemical properties and poly (rA) binding", Nucleic Acids Research 15(16):6625–6641.

Gordon, 1989, "Transgenic Animals", International Review of Cytology, 115:171–229.

Greenspan et al, 1993, "Idiotypes: structure and immunogenicity", FASEB Journal 7:437–444.

Gu et al, 1994, "Deletion of a DNA Polymerase β Gene Segment in T Cells Using Cell Type–Specific Gene Targeting", Science 265:103–106.

Gurley et al, 1986, "Upstream Sequences Required for Efficient Expression of a Soybean Heat Shock Gene", Mol. & Cell. Biology 6(2):559–565.

Huse et al, 1989, "Generation of a Large Combinatorial Library of the Immunoglobulin Repertoire in Phage Lambda", Science 246:1275–1281.

Huston et al, 1988, "Protein engineering of antibody binding sites Recovery of specific activity in an anti–digoxin single–chain Fv analogue produced in *Escherichia coli*", Proc Natl. Acad. Sci USA 85:5879–5883.

Houghten et al, 1991, "Generation and use of synthetic peptide combinatorial libraries for basic research and drug discovery", Nature 354:84–86.

Inoue et al, 1987, "Sequence–dependent hydrolysis of RNA using modified oligonucleotide splints and R Nase H", FEBS Letters 215(2):327–330.

Inoue et al, 1987, "Synthesis and hybridization studies on two complementary nona(2'–O–methyl)ribonucleotides", Nucleic Acids Research 15(15):6131–6149.

Inouye et al., 1985, "Up–promoter mutations in the lpp gene of *Escherichia coli*", Nucleic Acids Research 13(9)3101–3110.

Irwin, 1968, "Comprehensive Observational Assessment: la. A Systematic. Quantitative Procedure for Assessing the Behavioral and Physiologic State of the Mouse", Psychopharmacologia 13:222–257.

Janknecht et al, 1991, "Rapid and efficient purification of native histidine–tagged protein expressed by recombinant vaccinia virus", PNAS 88:8972–8976.

Kohler et al., 1975, "Continuous cultures of fused cells secreting antibody of predefined specificity", Nature 256:495–497.

Lasko et al, 1992, "Targeted oncogene activation by site–specific recombination in transgenic mice", Proc. Natl. Acad. Sci. USA 89:6232–6236.

Lam et al, 1991, "A new type of synthetic peptide library for identifying ligand–binding activity", Nature 354:82–84.

Lavitrano et al, 1989, "Sperm Cells as Vectors for Introducing Foreign DNA into Eggs: Genetic Transformation of Mice", Cell 57:717–723.

Lewis et al, 1989, "Automated site–directed drug design: the formation of molecular templates in primary structure generation", Proc. R. Soc. Lond. B 236:141–162.

Lo, 1983, "Transformation by Iontophoretic Microinjection of DNA: Multiple Integrations without Tandem Insertions", Mol. & Cell. Biology 3(10):1803–1814.

Logan et al, 1984, "Adenovirus tripartite leader sequence enhances translation of mRNAs late after infection", Proc. Natl. Acad. Sci. USA 81:3655–3659.

Lowy et al, 1980, "Isolation of Transforming DNA: Cloning the Hamster aprt Gene", Cell 22:817–823.

Luo et al, 1997, "Mammalian Two–Hybrid System: A Complimentary Approach to the Yeast Two–Hybrid System", BioTechniques. 22:350–352.

McKinlay et al, 1989, "Rational Design of Antiviral Agents", Annu. Rev. Pharmacol. Toxicol. 29: 111–122.

Morrison et al, 1984, "Chimeric human antibody molecules Mouse antigen–binding domains with human constant region domains", Proc Natl. Acad Sci USA 81:6851–6855.

Mulligan et al, 1981, "Selection for animal cells that express the *Escherichia coli* gene coding for xanthine–guanine phosphoribosyltransferase", Proc. Natl. Acad. Sci. USA 78(4):2072–2076.

Nagy 2000, "Precision and Accuracy of Dual–Energy X–ray Absorptiometry for Determining in Vivo Body Composition of Mice." Obesity Research, vol. 8 No. 5, pg. 392–398.

Neuberger et al, 1984, "Recombinant antibodies possessing novel effector functions", Nature 312:604–608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Ripka, 1998, "Computers picture the perfect drug", New Scientist.

Ruther et al, 1983, "Easy identification of cDNA clones", EMBO Journal 2(10):1791–1794.

Santerre et al, 1984, "Expression of prokaryotic genes for hygromycin B and G418 resistance as dominant–selection markers in mouse L cells", Gene 30: 147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the Autographa californica Nuclear Polyhedrosis Virus Genome Deletion Mutations within the Polyhedrin Gene", J. Virol. 46(2):584–593.

Songyang et al, 1993, "SH2 Domains Recognize Specific Phosphopeptide Sequences", Cell 72:767–778.

Stein et al, 1988, "Physiochemical properties of phosphorothioate oligodeoxynucleotides", Nucleic Acids Research 16(8):3209–3221.

Szybalska et al, 1962, "Genetics of Human Cell Lines. IV. DNA–Mediated Heritable Transformation of a Biochemical Trait", Proc. Natl. Acad. Sci. USA 48:2026–2034.

Takamatsu et al, 1987, "Expression of bacterial chloramphenicol acetyltransferase gene in tobacco plants mediated by TMV–RNA", EMBO Journal 6(2):307–311.

Takeda et al, 1985, "Construction of chimaeric processed immunoglobulin genes containing mouse variable and human constant region sequences", Nature 314:452–454.

Thompson et al, 1989, "Germ Line Transmission and Expression of a Corrected HPRT Gene Produced by Gene Targeting in Embryonic Stem Cells", Cell 56:313–321.

Van Der Putten et al, 1985, "Efficient insertion of genes into the mouse germ line via retroviral vectors", Proc. Natl. Acad. Sci USA 82:6148–6152.

Van Heeke et al, 1989, "Expression of Human Asparagine Synthetase in *Escherichia coli*", J. Biol. Chemistry 264(10):5503–5509.

Ward et al, 1989, "Binding activities of a repetoire of single immunoglobulin variable domains secreted from *Escherichia coli*", Nature 341:544–546.

Wigler et al, 1977, "Transfer of Purified Herpes Virus Thymidine Kinase Gene to Cultured Mouse Cells", Cell 11:223–232.

Wigler et al, 1980, "Transformation of mammalian cells with an amplifiable dominant–acting gene", Proc. Natl. Acad. Sci. USA 77(6):3567–3570.

SEQUENCE LISTING

<160> NUMBER OF SEQ ID NOS: 9

<210> SEQ ID NO 1
<211> LENGTH: 2220
<212> TYPE: DNA
<213> ORGANISM: homo sapiens

<400> SEQUENCE: 1
atgctgtact ccccagggcc gagtcttccg gagtcagcag agagcctgga tggatcacag      60

-continued

```
gaggataagc ctcgggctc atgtgcggag cccacttta ctgatacggg aatggtggct      120
cacataaaca acagccggct caaggccaag ggcgtgggcc agcacgacaa cgcccagaac    180
tttggtaacc agagctttga ggagctgcga gcagcctgtc taagaaaggg ggagctcttc    240
gaggacccct tattccctgc tgaacccagc tcactgggct tcaaggacct gggccccaac    300
tccaaaaatg tgcagaacat ctcctggcag cggcccaagg atatcataaa caaccctcta    360
ttcatcatgg atgggatttc tccaacagac atctgccagg ggatcctcgg ggactgctgg    420
ctgctggctg ccatcggctc ccttaccacc tgccccaaac tgctataccg cgtggtgccc    480
agaggacaga gcttcaagaa aaactatgct ggcatcttcc attttcagat tggcagtttt    540
ggacagtggg tgaacgtggt ggtagatgac cggctgccca caagaatga caagctggtg     600 tttgtgcact caaccgaacg cagtgagttc tggagtgccc tgctggagaa ggcgtatgcc    660
aagctgagtg ggtcctatga agcattgtca gggggcagta ccatggaggg ccttgaggac    720
ttcacaggag gcgtggccca gagcttccaa ctccagaggc cccctcagaa cctgctcagg    780
ctccttagga aggccgtgga gcgatcctcc ctcatgggtt gctccattga agtcaccagt    840
gatagtgaac tggaatccat gactgacaag atgctggtga gagggcacgc ttactctgtg    900
actggccttc aggatgtcca ctacagaggc aaaatggaaa cactgattcg ggtccggaat    960 ccctgggcc ggattgagtg gaatggagct tggagtgaca gtgccaggga gtgggaagag   1020
gtggcctcag acatccagat gcagctgctg cacaagacgg aggacgggga gttctggatg   1080
tcctaccaag atttcctgaa caacttcacg ctcctggaga tctgcaacct cacgcctgat   1140
acactctctg gggactacaa gagctactgg cacaccacct tctacagggg cagctggcgc   1200
agaggcagct ccgcagggg ctgcaggaac cacccctggca cgttctggac caaccccag    1260 tttaagatct ctcttcctga gggggatgac ccagaggatg acgcagaggg caatgttgtg   1320
gtctgcacct gcctggtggc cctaatgcag aagaactggc ggcatgcacg gcagcaggga   1380
gcccagctgc agaccattgg ctttgtcctc tacgcggtcc caaaagagtt tcagaacatt   1440
caggatgtcc acttgaagaa ggaattcttc acgaagtatc aggaccacgg cttctcagag   1500
atcttcacca actcacggga ggtgagcagc caactccggc tgcctccggg ggaatatatc   1560
attattcccc ccacctttga gccacacaga atgctgact tcctgcttcg ggtcttcacc    1620
gagaagcaca gcgagtcatg ggaattggat gaagtcaact atgctgagca actccaagag   1680
gaaaaggtct ctgaggatga catggaccag gacttcctac atttgtttaa gatagtggca   1740
ggagagggca aggagatagg ggtgtatgag ctccagaggc tgctcaacag gatggccatc   1800
aaattcaaaa gcttcaagac caagggcttt ggcctggatg cttgccgctg catgatcaac   1860
ctcatggata aagatggctc tggcaagctg gggcttctag agttcaagat cctgtggaaa   1920
aaactcaaga atggatgga catcttcaga gagtgtgacc aggaccattc aggcaccttg   1980
aactcctatg agatgcgcct ggttattgag aaagcaggca tcaagctgaa caacaaggta   2040
atgcaggtcc tggtggccag gtatgcagat gatgacctga tcatagactt tgacagcttc   2100
atcagctgtt tcctgaggct aaagaccatg ttcacattct ttctaaccat ggaccccaag   2160
aatactggcc atatttgctt gagcctggaa cagtggctgc agatgaccat gtggggatag   2220
```

<210> SEQ ID NO 2
<211> LENGTH: 739
<212> TYPE: PRT
<213> ORGANISM: homo sapiens

<400> SEQUENCE: 2

-continued

```
Met Leu Tyr Ser Pro Gly Pro Ser Leu Pro Glu Ser Ala Glu Ser Leu
 1               5                  10                 15

Asp Gly Ser Gln Glu Asp Lys Pro Arg Gly Ser Cys Ala Glu Pro Thr
            20                  25                  30

Phe Thr Asp Thr Gly Met Val Ala His Ile Asn Asn Ser Arg Leu Lys
            35                  40                  45

Ala Lys Gly Val Gly Gln His Asp Asn Ala Gln Asn Phe Gly Asn Gln
        50                  55                  60

Ser Phe Glu Glu Leu Arg Ala Ala Cys Leu Arg Lys Gly Glu Leu Phe
65                  70                  75                  80

Glu Asp Pro Leu Phe Pro Ala Glu Pro Ser Ser Leu Gly Phe Lys Asp
                85                  90                  95

Leu Gly Pro Asn Ser Lys Asn Val Gln Asn Ile Ser Trp Gln Arg Pro
            100                 105                 110

Lys Asp Ile Ile Asn Asn Pro Leu Phe Ile Met Asp Gly Ile Ser Pro
        115                 120                 125

Thr Asp Ile Cys Gln Gly Ile Leu Gly Asp Cys Trp Leu Leu Ala Ala
        130                 135                 140

Ile Gly Ser Leu Thr Thr Cys Pro Lys Leu Leu Tyr Arg Val Val Pro
145                 150                 155                 160

Arg Gly Gln Ser Phe Lys Lys Asn Tyr Ala Gly Ile Phe His Phe Gln
                165                 170                 175

Ile Trp Gln Phe Gly Gln Trp Val Asn Val Val Asp Asp Arg Leu
            180                 185                 190

Pro Thr Lys Asn Asp Lys Leu Val Phe Val His Ser Thr Glu Arg Ser
        195                 200                 205

Glu Phe Trp Ser Ala Leu Leu Glu Lys Ala Tyr Ala Lys Leu Ser Gly
    210                 215                 220

Ser Tyr Glu Ala Leu Ser Gly Gly Ser Thr Met Glu Gly Leu Glu Asp
225                 230                 235                 240

Phe Thr Gly Gly Val Ala Gln Ser Phe Gln Leu Gln Arg Pro Pro Gln
                245                 250                 255

Asn Leu Leu Arg Leu Arg Lys Ala Val Glu Arg Ser Ser Leu Met
            260                 265                 270

Gly Cys Ser Ile Glu Val Thr Ser Asp Ser Glu Leu Glu Ser Met Thr
        275                 280                 285

Asp Lys Met Leu Val Arg Gly His Ala Tyr Ser Val Thr Gly Leu Gln
        290                 295                 300

Asp Val His Tyr Arg Gly Lys Met Glu Thr Leu Ile Arg Val Arg Asn
305                 310                 315                 320

Pro Trp Gly Arg Ile Glu Trp Asn Gly Ala Trp Ser Asp Ser Ala Arg
                325                 330                 335

Glu Trp Glu Glu Val Ala Ser Asp Ile Gln Met Gln Leu Leu His Lys
            340                 345                 350

Thr Glu Asp Gly Glu Phe Trp Met Ser Tyr Gln Asp Phe Leu Asn Asn
            355                 360                 365

Phe Thr Leu Leu Glu Ile Cys Asn Leu Thr Pro Asp Thr Leu Ser Gly
    370                 375                 380

Asp Tyr Lys Ser Tyr Trp His Thr Thr Phe Tyr Glu Gly Ser Trp Arg
385                 390                 395                 400

Arg Gly Ser Ser Ala Gly Gly Cys Arg Asn His Pro Gly Thr Phe Trp
                405                 410                 415
```

```
Thr Asn Pro Gln Phe Lys Ile Ser Leu Pro Glu Gly Asp Asp Pro Glu
            420                 425                 430
Asp Asp Ala Glu Gly Asn Val Val Cys Thr Cys Leu Val Ala Leu
        435                 440                 445
Met Gln Lys Asn Trp Arg His Ala Arg Gln Gln Gly Ala Gln Leu Gln
    450                 455                 460
Thr Ile Gly Phe Val Leu Tyr Ala Val Pro Lys Glu Phe Gln Asn Ile
465                 470                 475                 480
Gln Asp Val His Leu Lys Lys Glu Phe Phe Thr Lys Tyr Gln Asp His
                485                 490                 495
Gly Phe Ser Glu Ile Phe Thr Asn Ser Arg Glu Val Ser Ser Gln Leu
            500                 505                 510
Arg Leu Pro Pro Gly Glu Tyr Ile Ile Pro Ser Thr Phe Glu Pro
        515                 520                 525
His Arg Asp Ala Asp Phe Leu Leu Arg Val Phe Thr Glu Lys His Ser
    530                 535                 540
Glu Ser Trp Glu Leu Asp Glu Val Asn Tyr Ala Glu Gln Leu Gln Glu
545                 550                 555                 560
Glu Lys Val Ser Glu Asp Met Asp Gln Asp Phe Leu His Leu Phe
                565                 570                 575
Lys Ile Val Ala Gly Glu Gly Lys Glu Ile Gly Val Tyr Glu Leu Gln
            580                 585                 590
Arg Leu Leu Asn Arg Met Ala Ile Lys Phe Lys Ser Phe Lys Thr Lys
        595                 600                 605
Gly Phe Gly Leu Asp Ala Cys Arg Cys Met Ile Asn Leu Met Asp Lys
    610                 615                 620
Asp Gly Ser Gly Lys Leu Gly Leu Leu Glu Phe Lys Ile Leu Trp Lys
625                 630                 635                 640
Lys Leu Lys Lys Trp Met Asp Ile Phe Arg Glu Cys Asp Gln Asp His
                645                 650                 655
Ser Gly Thr Leu Asn Ser Tyr Glu Met Arg Leu Val Ile Glu Lys Ala
            660                 665                 670
Gly Ile Lys Leu Asn Asn Lys Val Met Gln Val Leu Val Ala Arg Tyr
        675                 680                 685
Ala Asp Asp Asp Leu Ile Ile Asp Phe Asp Ser Phe Ile Ser Cys Phe
    690                 695                 700
Leu Arg Leu Lys Thr Met Phe Thr Phe Phe Leu Thr Met Asp Pro Lys
705                 710                 715                 720
Asn Thr Gly His Ile Cys Leu Ser Leu Glu Gln Trp Leu Gln Met Thr
                725                 730                 735
Met Trp Gly

<210> SEQ ID NO 3
<211> LENGTH: 2172
<212> TYPE: DNA
<213> ORGANISM: homo sapiens

<400> SEQUENCE: 3
atgctgtact cccagggcc gagtcttccg gagtcagcag agagcctgga tggatcacag      60
gaggataagc ctcggggctc atgtgcggag cccactttta ctgatacggg aatggtggct    120
cacataaaca acagccggct caaggccaag ggcgtgggcc agcacgacaa cgcccagaac    180
tttggtaacc agagctttga ggagctgcga gcagcctgtc aagaaagggg ggagctcttc    240
gaggacccct tattccctgc tgaacccagc tcactgggct tcaaggacct gggccccaac    300
```

```
tccaaaaatg tgcagaacat ctcctggcag cggcccaagg atatcataaa caaccctcta    360
ttcatcatgg atgggatttc tccaacagac atctgccagg ggatcctcgg ggactgctgg    420
ctgctggctg ccatcggctc ccttaccacc tgccccaaac tgctataccg cgtggtgccc    480
agaggacaga gcttcaagaa aaactatgct ggcatcttcc attttcagat ttggcagttt    540
ggacagtggg tgaacgtggt ggtagatgac cggctgccca caaagaatga caagctggtg    600
tttgtgcact caaccgaacg cagtgagttc tggagtgccc tgctggagaa ggcgtatgcc    660
aagctgagtg ggtcctatga agcattgtca gggggcagta ccatggaggg ccttgaggac    720
ttcacaggag gcgtggccca gagcttccaa ctccagaggc cccctcagaa cctgctcagg    780
ctccttagga aggccgtgga gcgatcctcc ctcatgggtt gctccattga agtcaccagt    840
gatagtgaac tggaatccat gactgacaag atgctggtga gagggcacgc ttactctgtg    900
actggccttc aggatgtcca ctacagaggc aaaatgaaaa cactgattcg ggtccggaat    960
ccctggggcc ggattgagtg gaatggagct tggagtgaca gtgccaggga gtgggaagag   1020
gtggcctcag acatccagat gcagctgctg cacaagacgg aggacgggga gttctggatg   1080
tcctaccaag atttcctgaa caacttcacg ctcctggaga tctgcaacct cacgcctgat   1140
acactctctg ggactacaa gagctactgg cacaccacct tctacgaggg cagctggcgc    1200
agaggcagct ccgcaggggg ctgcaggaac caccctggca cgttctggac caaccccag    1260
tttaagatct ctcttcctga ggggatgac ccagaggatg acgcagaggg caatgttgtg    1320
gtctgcacct gcctggtggc cctaatgcag aagaactggc ggcatgcacg gcagcaggga   1380
gcccagctgc agaccattgg ctttgtcctc tacgcggtcc caaagagtt tcagaacatt    1440
caggatgtcc acttgaagaa ggaattcttc acgaagtatc aggaccacgg cttctcagag   1500
atcttcacca actcacggga ggtgagcagc caactccggc tgcctccggg ggaatatatc   1560
attattccct ccacctttga gccacacaga gatgctgact tcctgcttcg ggtcttcacc   1620
gagaagcaca gcgagtcatg ggaattggat gaagtcaact atgctgagca actccaagag   1680
gaaaaggtct ctgaggatga catggaccag gacttcctac atttgtttaa gatagtggca   1740
ggagagggca aggagatagg ggtgtatgag ctccagaggc tgctcaacag gatggccatc   1800
aaattcaaaa gcttcaagac caagggcttt ggcctggatg cttgccgctg catgatcaac   1860
ctcatggata agatggctc tggcaagctg gggcttctag agttcaagat cctgtggaaa   1920
aaactcaaga aatggatgga catcttcaga gagtgtgacc aggaccattc aggcaccttg   1980
aactcctatg agatgcgcct ggttattgag aaagcaggca tcaagctgaa caacaaggta   2040
atgcaggtcc tggtggccag gtatgcagat gatgacctga tcatagactt tgacagcttc   2100
atcagctgtt tcctgaggct aaagaccatg ttcatggctg cagatgacca tgtggggata   2160
gaggcgctgt ag                                                        2172
```

<210> SEQ ID NO 4
<211> LENGTH: 723
<212> TYPE: PRT
<213> ORGANISM: homo sapiens

<400> SEQUENCE: 4

Met Leu Tyr Ser Pro Gly Pro Ser Leu Pro Glu Ser Ala Glu Ser Leu
1               5                   10                  15

Asp Gly Ser Gln Glu Asp Lys Pro Arg Gly Ser Cys Ala Glu Pro Thr
            20                  25                  30

-continued

```
Phe Thr Asp Thr Gly Met Val Ala His Ile Asn Asn Ser Arg Leu Lys
        35                  40                  45

Ala Lys Gly Val Gly Gln His Asp Asn Ala Gln Asn Phe Gly Asn Gln
        50                  55                  60

Ser Phe Glu Glu Leu Arg Ala Ala Cys Leu Arg Lys Gly Glu Leu Phe
65                  70                  75                  80

Glu Asp Pro Leu Phe Pro Ala Glu Pro Ser Ser Leu Gly Phe Lys Asp
                85                  90                  95

Leu Gly Pro Asn Ser Lys Asn Val Gln Asn Ile Ser Trp Gln Arg Pro
                100                 105                 110

Lys Asp Ile Ile Asn Asn Pro Leu Phe Ile Met Asp Gly Ile Ser Pro
                115                 120                 125

Thr Asp Ile Cys Gln Gly Ile Leu Gly Asp Cys Trp Leu Leu Ala Ala
    130                 135                 140

Ile Gly Ser Leu Thr Thr Cys Pro Lys Leu Leu Tyr Arg Val Val Pro
145                 150                 155                 160

Arg Gly Gln Ser Phe Lys Lys Asn Tyr Ala Gly Ile Phe His Phe Gln
                165                 170                 175

Ile Trp Gln Phe Gly Gln Trp Val Asn Val Val Asp Asp Arg Leu
                180                 185                 190

Pro Thr Lys Asn Asp Lys Leu Val Phe Val His Ser Thr Glu Arg Ser
                195                 200                 205

Glu Phe Trp Ser Ala Leu Leu Glu Lys Ala Tyr Ala Lys Leu Ser Gly
    210                 215                 220

Ser Tyr Glu Ala Leu Ser Gly Gly Ser Thr Met Glu Gly Leu Glu Asp
225                 230                 235                 240

Phe Thr Gly Gly Val Ala Gln Ser Phe Gln Leu Gln Arg Pro Pro Gln
                245                 250                 255

Asn Leu Leu Arg Leu Leu Arg Lys Ala Val Glu Arg Ser Ser Leu Met
                260                 265                 270

Gly Cys Ser Ile Glu Val Thr Ser Asp Ser Glu Leu Glu Ser Met Thr
    275                 280                 285

Asp Lys Met Leu Val Arg Gly His Ala Tyr Ser Val Thr Gly Leu Gln
290                 295                 300

Asp Val His Tyr Arg Gly Lys Met Glu Thr Leu Ile Arg Val Arg Asn
305                 310                 315                 320

Pro Trp Gly Arg Ile Glu Trp Asn Gly Ala Trp Ser Asp Ser Ala Arg
                325                 330                 335

Glu Trp Glu Glu Val Ala Ser Asp Ile Gln Met Gln Leu Leu His Lys
            340                 345                 350

Thr Glu Asp Gly Glu Phe Trp Met Ser Tyr Gln Asp Phe Leu Asn Asn
            355                 360                 365

Phe Thr Leu Leu Glu Ile Cys Asn Leu Thr Pro Asp Thr Leu Ser Gly
    370                 375                 380

Asp Tyr Lys Ser Tyr Trp His Thr Thr Phe Tyr Glu Gly Ser Trp Arg
385                 390                 395                 400

Arg Gly Ser Ser Ala Gly Gly Cys Arg Asn His Pro Gly Thr Phe Trp
                405                 410                 415

Thr Asn Pro Gln Phe Lys Ile Ser Leu Pro Glu Gly Asp Asp Pro Glu
                420                 425                 430

Asp Asp Ala Glu Gly Asn Val Val Val Cys Thr Cys Leu Val Ala Leu
    435                 440                 445

Met Gln Lys Asn Trp Arg His Ala Arg Gln Gln Gly Ala Gln Leu Gln
```

```
      450              455              460
Thr Ile Gly Phe Val Leu Tyr Ala Val Pro Lys Glu Phe Gln Asn Ile
465              470              475              480

Gln Asp Val His Leu Lys Lys Glu Phe Phe Thr Lys Tyr Gln Asp His
            485              490              495

Gly Phe Ser Glu Ile Phe Thr Asn Ser Arg Glu Val Ser Ser Gln Leu
            500              505              510

Arg Leu Pro Pro Gly Glu Tyr Ile Ile Ile Pro Ser Thr Phe Glu Pro
            515              520              525

His Arg Asp Ala Asp Phe Leu Leu Arg Val Phe Thr Glu Lys His Ser
            530              535              540

Glu Ser Trp Glu Leu Asp Glu Val Asn Tyr Ala Glu Gln Leu Gln Glu
545              550              555              560

Glu Lys Val Ser Glu Asp Asp Met Asp Gln Asp Phe Leu His Leu Phe
            565              570              575

Lys Ile Val Ala Gly Glu Gly Lys Glu Ile Gly Val Tyr Glu Leu Gln
            580              585              590

Arg Leu Leu Asn Arg Met Ala Ile Lys Phe Lys Ser Phe Lys Thr Lys
            595              600              605

Gly Phe Gly Leu Asp Ala Cys Arg Cys Met Ile Asn Leu Met Asp Lys
610              615              620

Asp Gly Ser Gly Lys Leu Gly Leu Leu Glu Phe Lys Ile Leu Trp Lys
625              630              635              640

Lys Leu Lys Lys Trp Met Asp Ile Phe Arg Glu Cys Asp Gln Asp His
            645              650              655

Ser Gly Thr Leu Asn Ser Tyr Glu Met Arg Leu Val Ile Glu Lys Ala
            660              665              670

Gly Ile Lys Leu Asn Asn Lys Val Met Gln Val Leu Val Ala Arg Tyr
            675              680              685

Ala Asp Asp Asp Leu Ile Ile Asp Phe Asp Ser Phe Ile Ser Cys Phe
            690              695              700

Leu Arg Leu Lys Thr Met Phe Met Ala Ala Asp Asp His Val Gly Ile
705              710              715              720

Glu Ala Leu

<210> SEQ ID NO 5
<211> LENGTH: 2109
<212> TYPE: DNA
<213> ORGANISM: homo sapiens

<400> SEQUENCE: 5
atggtggctc acataaacaa cagccggctc aaggccaagg gcgtgggcca gcacgacaac    60
gcccagaact tggtaaccca gagctttgag gagctgcgag cagcctgtct aagaaagggg   120
gagctcttcg aggacccctt attccctgct gaacccagct cactgggctt caaggacctg   180
ggccccaact ccaaaaatgt gcagaacatc tcctggcagc ggcccaagga tatcataaac   240
aaccctctat tcatcatgga tgggatttct ccaacagaca tctgccaggg gatcctcggg   300
gactgctggc tgctggctgc catcggctcc cttaccacct gccccaaact gctataccgc   360
gtggtgccca gaggacagag cttcaagaaa aactatgctg catcttcca ttttcagatt   420 tggcagtttg gacagtgggt gaacgtggtg gtagatgacc ggctgcccac aaagaatgac   480
aagctggtgt ttgtgcactc aaccgaacgc agtgagttcg gagtgccct gctggagaag   540 gcgtatgcca agctgagtgg gtcctatgaa gcattgtcag ggggcagtac catggagggc   600
```

```
cttgaggact tcacaggagg cgtggcccag agcttccaac tccagaggcc ccctcagaac    660
ctgctcaggc tccttaggaa ggccgtggag cgatcctccc tcatgggttg ctccattgaa    720
gtcaccagtg atagtgaact ggaatccatg actgacaaga tgctggtgag agggcacgct    780
tactctgtga ctggccttca ggatgtccac tacagaggca aaatggaaac actgattcgg    840
gtccggaatc cctggggccg gattgagtgg aatggagctt ggagtgacag tgccagggag    900
tgggaagagg tggcctcaga catccagatg cagctgctgc acaagacgga ggacggggag    960
ttctggatgt cctaccaaga tttcctgaac aacttcacgc tcctggagat ctgcaacctc   1020
acgcctgata cactctctgg ggactacaag agctactggc acaccacctt ctacagggc    1080
agctggcgca gaggcagctc cgcagggggc tgcaggaacc ccctggcac gttctggacc    1140
aaccccagt ttaagatctc tcttcctgag ggggatgacc cagaggatga cgcagagggc    1200
aatgttgtgg tctgcacctg cctggtggcc ctaatgcaga agaactggcg gcatgcacgg   1260
cagcagggag cccagctgca gaccattggc tttgtcctct acgcggtccc aaaagagttt   1320
cagaacattc aggatgtcca cttgaagaag gaattcttca cgaagtatca ggaccacggc   1380
ttctcagaga tcttcaccaa ctcacgggag gtgagcagcc aactccggct gcctccgggg   1440
gaatatatca ttattccctc cacctttgag ccacacagag atgctgactt cctgcttcgg   1500
gtcttcaccg agaagcacag cgagtcatgg gaattggatg aagtcaacta tgctgagcaa   1560
ctccaagagg aaaaggtctc tgaggatgac atggaccagg acttcctaca tttgtttaag   1620
atagtggcag gagagggcaa ggagataggg gtgtatgagc tccagaggct gctcaacagg   1680
atggccatca aattcaaaag cttcaagacc aagggctttg gcctggatgc ttgccgctgc   1740
atgatcaacc tcatggataa agatggctct ggcaagctgg ggcttctaga gttcaagatc   1800
ctgtggaaaa aactcaagaa atggatggac atcttcagag agtgtgacca ggaccattca   1860
ggcaccttga actcctatga tgcgcctg gttattgaga aagcaggcat caagctgaac   1920
aacaaggtaa tgcaggtcct ggtggccagg tatgcagatg atgacctgat catagacttt   1980
gacagcttca tcagctgttt cctgaggcta aagaccatgt tcacattctt tctaaccatg   2040
gaccccaaga atactggcca tatttgcttg agcctggaac agtggctgca gatgaccatg   2100
tggggatag                                                         2109

<210> SEQ ID NO 6
<211> LENGTH: 702
<212> TYPE: PRT
<213> ORGANISM: homo sapiens

<400> SEQUENCE: 6

Met Val Ala His Ile Asn Asn Ser Arg Leu Lys Ala Lys Gly Val Gly
  1               5                  10                  15

Gln His Asp Asn Ala Gln Asn Phe Gly Asn Gln Ser Phe Glu Glu Leu
                 20                  25                  30

Arg Ala Ala Cys Leu Arg Lys Gly Glu Leu Phe Glu Asp Pro Leu Phe
             35                  40                  45

Pro Ala Glu Pro Ser Ser Leu Gly Phe Lys Asp Leu Gly Pro Asn Ser
         50                  55                  60

Lys Asn Val Gln Asn Ile Ser Trp Gln Arg Pro Lys Asp Ile Ile Asn
 65                  70                  75                  80

Asn Pro Leu Phe Ile Met Asp Gly Ile Ser Pro Thr Asp Ile Cys Gln
                 85                  90                  95
```

```
Gly Ile Leu Gly Asp Cys Trp Leu Leu Ala Ile Gly Ser Leu Thr
            100                 105                 110

Thr Cys Pro Lys Leu Leu Tyr Arg Val Pro Arg Gly Gln Ser Phe
            115                 120                 125

Lys Lys Asn Tyr Ala Gly Ile Phe His Phe Gln Ile Trp Gln Phe Gly
        130                 135                 140

Gln Trp Val Asn Val Val Asp Asp Arg Leu Pro Thr Lys Asn Asp
145                 150                 155                 160

Lys Leu Val Phe Val His Ser Thr Glu Arg Ser Glu Phe Trp Ser Ala
                165                 170                 175

Leu Leu Glu Lys Ala Tyr Ala Lys Leu Ser Gly Ser Tyr Glu Ala Leu
            180                 185                 190

Ser Gly Gly Ser Thr Met Glu Gly Leu Glu Asp Phe Thr Gly Gly Val
        195                 200                 205

Ala Gln Ser Phe Gln Leu Gln Arg Pro Pro Gln Asn Leu Leu Arg Leu
    210                 215                 220

Leu Arg Lys Ala Val Glu Arg Ser Ser Leu Met Gly Cys Ser Ile Glu
225                 230                 235                 240

Val Thr Ser Asp Ser Glu Leu Glu Ser Met Thr Asp Lys Met Leu Val
                245                 250                 255

Arg Gly His Ala Tyr Ser Val Thr Gly Leu Gln Asp Val His Tyr Arg
            260                 265                 270

Gly Lys Met Glu Thr Leu Ile Arg Val Arg Asn Pro Trp Gly Arg Ile
        275                 280                 285

Glu Trp Asn Gly Ala Trp Ser Asp Ser Ala Arg Glu Trp Glu Glu Val
    290                 295                 300

Ala Ser Asp Ile Gln Met Gln Leu Leu His Lys Thr Glu Asp Gly Glu
305                 310                 315                 320

Phe Trp Met Ser Tyr Gln Asp Phe Leu Asn Asn Phe Thr Leu Leu Glu
                325                 330                 335

Ile Cys Asn Leu Thr Pro Asp Thr Leu Ser Gly Asp Tyr Lys Ser Tyr
            340                 345                 350

Trp His Thr Thr Phe Tyr Glu Gly Ser Trp Arg Arg Gly Ser Ser Ala
        355                 360                 365

Gly Gly Cys Arg Asn His Pro Gly Thr Phe Trp Thr Asn Pro Gln Phe
    370                 375                 380

Lys Ile Ser Leu Pro Glu Gly Asp Asp Pro Glu Asp Ala Glu Gly
385                 390                 395                 400

Asn Val Val Cys Thr Cys Leu Val Ala Leu Met Gln Lys Asn Trp
                405                 410                 415

Arg His Ala Arg Gln Gln Gly Ala Gln Leu Gln Thr Ile Gly Phe Val
            420                 425                 430

Leu Tyr Ala Val Pro Lys Glu Phe Gln Asn Ile Gln Asp Val His Leu
        435                 440                 445

Lys Lys Glu Phe Phe Thr Lys Tyr Gln Asp His Gly Phe Ser Glu Ile
    450                 455                 460

Phe Thr Asn Ser Arg Glu Val Ser Ser Gln Leu Arg Leu Pro Pro Gly
465                 470                 475                 480

Glu Tyr Ile Ile Ile Pro Ser Thr Phe Glu Pro His Arg Asp Ala Asp
                485                 490                 495

Phe Leu Leu Arg Val Phe Thr Glu Lys His Ser Glu Ser Trp Glu Leu
            500                 505                 510

Asp Glu Val Asn Tyr Ala Glu Gln Leu Gln Glu Glu Lys Val Ser Glu
```

```
                515                 520                 525

Asp Asp Met Asp Gln Asp Phe Leu His Leu Phe Lys Ile Val Ala Gly
            530                 535                 540

Glu Gly Lys Glu Ile Gly Val Tyr Glu Leu Gln Arg Leu Leu Asn Arg
545                 550                 555                 560

Met Ala Ile Lys Phe Lys Ser Phe Lys Thr Lys Gly Phe Gly Leu Asp
                565                 570                 575

Ala Cys Arg Cys Met Ile Asn Leu Met Asp Lys Asp Gly Ser Gly Lys
            580                 585                 590

Leu Gly Leu Leu Glu Phe Lys Ile Leu Trp Lys Lys Leu Lys Lys Trp
            595                 600                 605

Met Asp Ile Phe Arg Glu Cys Asp Gln Asp His Ser Gly Thr Leu Asn
            610                 615                 620

Ser Tyr Glu Met Arg Leu Val Ile Glu Lys Ala Gly Ile Lys Leu Asn
625                 630                 635                 640

Asn Lys Val Met Gln Val Leu Val Ala Arg Tyr Ala Asp Asp Asp Leu
                645                 650                 655

Ile Ile Asp Phe Asp Ser Phe Ile Ser Cys Phe Leu Arg Leu Lys Thr
            660                 665                 670

Met Phe Thr Phe Phe Leu Thr Met Asp Pro Lys Asn Thr Gly His Ile
            675                 680                 685

Cys Leu Ser Leu Glu Gln Trp Leu Gln Met Thr Met Trp Gly
            690                 695                 700

<210> SEQ ID NO 7
<211> LENGTH: 2061
<212> TYPE: DNA
<213> ORGANISM: homo sapiens

<400> SEQUENCE: 7
atggtggctc acataaacaa cagccggctc aaggccaagg gcgtgggcca gcacgacaac      60
gcccagaact tggtaaccga gctttgag gagctgcgag cagcctgtct aagaaagggg       120
gagctcttcg aggacccctt attccctgct gaacccagct cactgggctt caaggacctg     180
ggccccaact ccaaaaatgt gcagaacatc tcctggcagc ggcccaagga tatcataaac     240
aaccctctat tcatcatgga tgggatttct ccaacagaca tctgccaggg gatcctcggg     300
gactgctggc tgctggctgc catcggctcc cttaccacct gccccaaact gctataccgc     360
gtggtgccca gaggacagag cttcaagaaa aactatgctg gcatcttcca ttttcagatt     420
tggcagtttg gacagtgggt gaacgtggtg gtagatgacc ggctgcccac aaagaatgac     480
aagctggtgt ttgtgcactc aaccgaacgc agtgagttct ggagtgccct gctggagaag     540
gcgtatgcca agctgagtgg gtcctatgaa gcattgtcag gggcagtac catggagggc      600 cttgaggact tcacaggagg cgtggcccag agcttccaac tccagaggcc ccctcagaac     660
ctgctcaggc tccttaggaa ggccgtggag cgatcctccc tcatggggtt ctccattgaa     720
gtcaccagtg atagtgaact ggaatccatg actgacaaga tgctggtgag agggcacgct     780
tactctgtga ctggccttca ggatgtccac tacagaggca aaatggaaac actgattcgg     840
gtccggaatc cctggggccg gattgagtgg aatggagctt ggagtgacag tgccagggag     900
tgggaagagg tggcctcaga catccagatg cagctgctgc acaagacgga ggacggggag     960
ttctggatgt cctaccaaga tttcctgaac aacttcacgc tcctggagat ctgcaacctc    1020
acgcctgata cactctctgg ggactacaag agctactggc acaccacctt ctacgagggc    1080
```

```
agctggcgca gaggcagctc cgcagggggc tgcaggaacc accctggcac gttctggacc   1140 aaccccagt ttaagatctc tcttcctgag ggggatgacc cagaggatga cgcagagggc    1200
aatgttgtgg tctgcacctg cctggtggcc ctaatgcaga agaactggcg gcatgcacgg   1260
cagcagggag cccagctgca gaccattggc tttgtcctct acgcggtccc aaaagagttt   1320
cagaacattc aggatgtcca cttgaagaag gaattcttca cgaagtatca ggaccacggc   1380
ttctcagaga tcttcaccaa ctcacgggag gtgagcagcc aactccggct gcctccgggg   1440
gaatatatca ttattccctc cacctttgag ccacacagag atgctgactt cctgcttcgg   1500
gtcttcaccg agaagcacag cgagtcatgg gaattggatg aagtcaacta tgctgagcaa   1560
ctccaagagg aaaaggtctc tgaggatgac atggaccagg acttcctaca tttgtttaag   1620
atagtggcag gagagggcaa ggagataggg gtgtatgagc tccagaggct gctcaacagg   1680
atggccatca aattcaaaag cttcaagacc aagggctttg cctggatgc ttgccgctgc    1740 atgatcaacc tcatggataa agatggctct ggcaagctgg ggcttctaga gttcaagatc   1800
ctgtggaaaa aactcaagaa atggatggac atcttcagag agtgtgacca ggaccattca   1860
ggcaccttga actcctatga gatgcgcctg gttattgaga aagcaggcat caagctgaac   1920
aacaaggtaa tgcaggtcct ggtggccagg tatgcagatg atgacctgat catagacttt   1980
gacagcttca tcagctgttt cctgaggcta aagaccatgt tcatggctgc agatgaccat   2040
gtggggatag aggcgctgta g                                             2061

<210> SEQ ID NO 8
<211> LENGTH: 686
<212> TYPE: PRT
<213> ORGANISM: homo sapiens

<400> SEQUENCE: 8

Met Val Ala His Ile Asn Asn Ser Arg Leu Lys Ala Lys Gly Val Gly
 1               5                  10                  15

Gln His Asp Asn Ala Gln Asn Phe Gly Asn Gln Ser Phe Glu Glu Leu
            20                  25                  30

Arg Ala Ala Cys Leu Arg Lys Gly Glu Leu Phe Glu Asp Pro Leu Phe
        35                  40                  45

Pro Ala Glu Pro Ser Ser Leu Gly Phe Lys Asp Leu Gly Pro Asn Ser
    50                  55                  60

Lys Asn Val Gln Asn Ile Ser Trp Gln Arg Pro Lys Asp Ile Ile Asn
65                  70                  75                  80

Asn Pro Leu Phe Ile Met Asp Gly Ile Ser Pro Thr Asp Ile Cys Gln
                85                  90                  95

Gly Ile Leu Gly Asp Cys Trp Leu Leu Ala Ala Ile Gly Ser Leu Thr
            100                 105                 110

Thr Cys Pro Lys Leu Leu Tyr Arg Val Val Pro Arg Gly Gln Ser Phe
        115                 120                 125

Lys Lys Asn Tyr Ala Gly Ile Phe His Phe Gln Ile Trp Gln Phe Gly
    130                 135                 140

Gln Trp Val Asn Val Val Asp Asp Arg Leu Pro Thr Lys Asn Asp
145                 150                 155                 160

Lys Leu Val Phe Val His Ser Thr Glu Arg Ser Glu Phe Trp Ser Ala
                165                 170                 175

Leu Leu Glu Lys Ala Tyr Ala Lys Leu Ser Gly Ser Tyr Glu Ala Leu
            180                 185                 190

Ser Gly Gly Ser Thr Met Glu Gly Leu Glu Asp Phe Thr Gly Gly Val
```

-continued

```
            195                 200                 205
Ala Gln Ser Phe Gln Leu Gln Arg Pro Pro Gln Asn Leu Leu Arg Leu
    210                 215                 220
Leu Arg Lys Ala Val Glu Arg Ser Ser Leu Met Gly Cys Ser Ile Glu
225                 230                 235                 240
Val Thr Ser Asp Ser Glu Leu Glu Ser Met Thr Asp Lys Met Leu Val
                245                 250                 255
Arg Gly His Ala Tyr Ser Val Thr Gly Leu Gln Asp Val His Tyr Arg
            260                 265                 270
Gly Lys Met Glu Thr Leu Ile Arg Val Arg Asn Pro Trp Gly Arg Ile
        275                 280                 285
Glu Trp Asn Gly Ala Trp Ser Asp Ser Ala Arg Glu Trp Glu Val
    290                 295                 300
Ala Ser Asp Ile Gln Met Gln Leu Leu His Lys Thr Glu Asp Gly Glu
305                 310                 315                 320
Phe Trp Met Ser Tyr Gln Asp Phe Leu Asn Asn Phe Thr Leu Leu Glu
                325                 330                 335
Ile Cys Asn Leu Thr Pro Asp Thr Leu Ser Gly Asp Tyr Lys Ser Tyr
            340                 345                 350
Trp His Thr Thr Phe Tyr Glu Gly Ser Trp Arg Arg Gly Ser Ser Ala
        355                 360                 365
Gly Gly Cys Arg Asn His Pro Gly Thr Phe Trp Thr Asn Pro Gln Phe
370                 375                 380
Lys Ile Ser Leu Pro Glu Gly Asp Asp Pro Glu Asp Asp Ala Glu Gly
385                 390                 395                 400
Asn Val Val Cys Thr Cys Leu Val Ala Leu Met Gln Lys Asn Trp
                405                 410                 415
Arg His Ala Arg Gln Gln Gly Ala Gln Leu Gln Thr Ile Gly Phe Val
            420                 425                 430
Leu Tyr Ala Val Pro Lys Glu Phe Gln Asn Ile Gln Asp Val His Leu
        435                 440                 445
Lys Lys Glu Phe Phe Thr Lys Tyr Gln Asp His Gly Phe Ser Glu Ile
    450                 455                 460
Phe Thr Asn Ser Arg Glu Val Ser Ser Gln Leu Arg Leu Pro Pro Gly
465                 470                 475                 480
Glu Tyr Ile Ile Ile Pro Ser Thr Phe Glu Pro His Arg Asp Ala Asp
                485                 490                 495
Phe Leu Leu Arg Val Phe Thr Glu Lys His Ser Glu Ser Trp Glu Leu
            500                 505                 510
Asp Glu Val Asn Tyr Ala Glu Gln Leu Gln Glu Lys Val Ser Glu
        515                 520                 525
Asp Asp Met Asp Gln Asp Phe Leu His Leu Phe Lys Ile Val Ala Gly
    530                 535                 540
Glu Gly Lys Glu Ile Gly Val Tyr Glu Leu Gln Arg Leu Leu Asn Arg
545                 550                 555                 560
Met Ala Ile Lys Phe Lys Ser Phe Lys Thr Lys Gly Phe Gly Leu Asp
                565                 570                 575
Ala Cys Arg Cys Met Ile Asn Leu Met Asp Lys Asp Gly Ser Gly Lys
            580                 585                 590
Leu Gly Leu Leu Glu Phe Lys Ile Leu Trp Lys Lys Leu Lys Lys Trp
        595                 600                 605
Met Asp Ile Phe Arg Glu Cys Asp Gln Asp His Ser Gly Thr Leu Asn
    610                 615                 620
```

```
Ser Tyr Glu Met Arg Leu Val Ile Glu Lys Ala Gly Ile Lys Leu Asn
625                 630                 635                 640

Asn Lys Val Met Gln Val Leu Val Ala Arg Tyr Ala Asp Asp Leu
            645                 650                 655

Ile Ile Asp Phe Asp Ser Phe Ile Ser Cys Phe Leu Arg Leu Lys Thr
                660                 665                 670

Met Phe Met Ala Ala Asp Asp His Val Gly Ile Glu Ala Leu
                675                 680                 685

<210> SEQ ID NO 9
<211> LENGTH: 2806
<212> TYPE: DNA
<213> ORGANISM: homo sapiens

<400> SEQUENCE: 9
```

| | | | | |
|---|---|---|---|---|
| caagcaccga | gctagccacc | agcatgctgt | actccccagg | gccgagtctt | ccggagtcag | 60 |
| cagagagcct | ggatggatca | caggaggata | agcctcgggg | ctcatgtgcg | gagcccactt | 120 |
| ttactgatac | gggaatggtg | gctcacataa | acaacagccg | gctcaaggcc | aagggcgtgg | 180 |
| gccagcacga | caacgcccag | aactttggta | ccagagcttt | gaggagctg | cgagcagcct | 240 |
| gtctaagaaa | ggggagctc | ttcgaggacc | ccttattccc | tgctgaaccc | agctcactgg | 300 |
| gcttcaagga | cctgggcccc | aactccaaaa | atgtgcagaa | catctcctgg | cagcggccca | 360 |
| aggatatcat | aaacaaccct | ctattcatca | tggatgggat | ttctccaaca | gacatctgcc | 420 |
| agggatcct | cggggactgc | tggctgctgg | ctgccatcgg | ctcccttacc | acctgcccca | 480 |
| aactgctata | ccgcgtggtg | cccagaggac | agagcttcaa | gaaaaactat | gctggcatct | 540 |
| tccattttca | gatttggcag | tttggacagt | gggtgaacgt | ggtggtagat | gaccggctgc | 600 |
| ccacaaagaa | tgacaagctg | gtgtttgtgc | actcaaccga | acgcagtgag | ttctggagtg | 660 |
| ccctgctgga | gaaggcgtat | gccaagctga | gtgggtccta | tgaagcattg | tcaggggca | 720 |
| gtaccatgga | gggccttgag | gacttcacag | gaggcgtggc | ccagagcttc | caactccaga | 780 |
| ggcccccctca | gaacctgctc | aggctcctta | ggaaggccgt | ggagcgatcc | tccctcatgg | 840 |
| gttgctccat | tgaagtcacc | agtgatagtg | aactggaatc | catgactgac | aagatgctgg | 900 |
| tgagagggca | cgcttactct | gtgactggcc | ttcaggatgt | ccactacaga | ggcaaaatgg | 960 |
| aaacactgat | tcgggtccgg | aatccctggg | gccggattga | gtggaatgga | gcttggagtg | 1020 |
| acagtgccag | ggagtgggaa | gaggtggcct | cagacatcca | gatgcagctg | ctgcacaaga | 1080 |
| cggaggacgg | ggagttctgg | atgtcctacc | aagatttcct | gaacaacttc | acgctcctgg | 1140 |
| agatctgcaa | cctcacgcct | gatacactct | ctggggacta | caagagctac | tggcacacca | 1200 |
| ccttctacga | gggcagctgg | cgcagaggca | gctccgcagg | gggctgcagg | aaccaccctg | 1260 |
| gcacgttctg | gaccaacccc | cagtttaaga | tctctcttcc | tgaggggat | gacccagagg | 1320 |
| atgacgcaga | gggcaatgtt | gtggtctgca | cctgcctggt | ggccctaatg | cagaagaact | 1380 |
| ggcggcatgc | acggcagcag | ggagcccagc | tgcagaccat | tggctttgtc | ctctacgcgg | 1440 |
| tcccaaaaga | gtttcagaac | attcaggatg | tccacttgaa | gaaggaattc | ttcacgaagt | 1500 |
| atcaggacca | cggcttctca | gagatcttca | ccaactcacg | ggaggtgagc | agccaactcc | 1560 |
| ggctgcctcc | gggggaatat | atcattattc | cctccacctt | tgagccacac | agagatgctg | 1620 |
| acttcctgct | tcgggtcttc | accgagaagc | acagcgagtc | atgggaattg | gatgaagtca | 1680 |
| actatgctga | gcaactccaa | gaggaaaagg | tctctgagga | tgacatggac | caggacttcc | 1740 |

-continued

```
tacatttgtt taagatagtg gcaggagagg gcaaggagat agggtgtat gagctccaga    1800
ggctgctcaa caggatggcc atcaaattca aaagcttcaa gaccaagggc tttggcctgg    1860
atgcttgccg ctgcatgatc aacctcatgg ataaagatgg ctctggcaag ctggggcttc    1920
tagagttcaa gatcctgtgg aaaaaactca agaaatggat ggacatcttc agagagtgtg    1980
accaggacca ttcaggcacc ttgaactcct atgagatgcg cctggttatt gagaaagcag    2040
gcatcaagct gaacaacaag gtaatgcagg tcctggtggc caggtatgca gatgatgacc    2100
tgatcataga ctttgacagc ttcatcagct gtttcctgag gctaaagacc atgttcacat    2160
tctttctaac catggacccc aagaatactg gccatatttg cttgagcctg aacagtggc     2220
tgcagatgac catgtgggga tagaggcgct gtaggagcct ggtcatctct accagcagca    2280
gcagcagcga ggttctagcc caggagggtg gggtgcttct tgtagccctc agctctccgg    2340
tctctgctga tgaaatgggc tccaggtggc agtgcccggg tcccaggtgc cgtgtttact    2400
gcagcagtgg gacctccgtg cccactcccc cagctcagag gctttctctt ttttccccaa    2460
cccggcttct gatggctggc tttcccccac catcgctctc tcagagtata ttttactaaa    2520
gagtagttga tgcttcccca gggtccccct ggctggggag gccaagaata gggaagggac    2580
ttgtagcccg tttcttaccc tccatgcttg ctgtcctgct cacacctacc tgctgaccac    2640
ccatcctggc acagcctctg ttttcctccc catctgtgga tactattcta ataaatagca    2700
catgccattg gcaaaaaaaa aaaaaaaaaa aaaaaaaaaa aaaaaaaaaa aaaaaaaaaa    2760
aaaaaaaaaa aaaaaaaaaa aaaaaaaaaa aaaaaaaaaa aaaaaa                    2806
```

HUMAN CALCIUM DEPENDENT PROTEASES, POLYNUCLEOTIDES ENCODING THE SAME, AND USES THEREOF

The present application is a continuation-in-part of U.S. application Ser. No. 09/653,839, filed on Sep. 1, 2000 now U.S. Pat. No. 6,433,153, which claims the benefit of U.S. Provisional Application Serial No. 60/152,057, filed Sep. 2, 1999, both of which are herein incorporated by reference in their entirety.

1.0 INTRODUCTION

The present invention relates to the discovery, identification, and characterization of novel human polynucleotides encoding proteins that share sequence similarity with human calcium dependent proteases, specifically calpains. The invention encompasses the described polynucleotides, host cell expression systems, the encoded proteins, fusion proteins, polypeptides and peptides, antibodies to the encoded proteins and peptides, and genetically engineered animals that either lack or overexpress the disclosed polynucleotides, antagonists and agonists of the proteins, and other compounds that modulate the expression or activity of the proteins encoded by the disclosed polynucleotides, which can be used for diagnosis, drug screening, clinical trial monitoring, the treatment of diseases and disorders, such as a reduced white blood cell count, and cosmetic or nutriceutical applications.

2.0 BACKGROUND OF THE INVENTION

Proteases are enzymes that mediate the proteolytic cleavage of polypeptide sequences. In particular, calcium-dependent proteases, such as calpains, have been found in virtually every vertebrate cell that has been examined for their presence. The calpain system has at least three well-characterized protein members that are activated in response to changes in calcium concentration. These proteins include at least two calpains that are activated at different concentrations of calcium, and a calpastatin that specifically inhibits the two calpains. Various tissue/species specific cDNAs have been described that are homologous to the calpains. Given the near ubiquitous expression of calpains, they have been implicated in a wide variety of cellular functions including, but not limited to, cell proliferation and differentiation, signal transduction, processes involving interactions between the cell membrane and cytoskeleton, secretion, platelet aggregation, cytokinesis, and disease. Accordingly, calpains represent a key target for the regulation of a variety of biological pathways.

Reduced white blood cell count, or neutropenia, is a major complication that occurs during many forms of chemotherapy, particularly those regimens involving myelosuppressive anti-cancer drugs, and as a result of certain infectious diseases. Although treatments for neutropenia currently exist in the art, they are not ideal for use in all circumstances, and are actually contraindicated in certain patients. Therefore, new treatments for neutropenia would represent a significant advance in the art.

3.0 SUMMARY OF THE INVENTION

The present invention relates to the discovery, identification, and characterization of nucleotides that encode novel human proteins, and the corresponding amino acid sequences of these proteins. The novel human proteins (NHPs) described for the first time herein share structural similarity with animal calcium-activated proteases, or calpains. As such, the novel genes represent a new class of protease proteins with a range of homologues and orthologs that transcend phyla and a broad range of species.

The novel human nucleic acid sequences described herein, encode proteins/open reading frames (ORFs) of 739, 723, 702, and 686 amino acids in length (see SEQ ID NOS:2, 4, 6, and 8 respectively).

The invention also encompasses agonists and antagonists of the described NHPs, including small molecules, large molecules, mutant NHPs, or portions thereof, that compete with native NHPs, peptides, and antibodies, as well as nucleotide sequences that can be used to inhibit the expression of the described NHPs (e.g., antisense and ribozyme molecules, and open reading frame or regulatory sequence replacement constructs) or to enhance the expression of the described NHPS (e.g., expression constructs that place the described polynucleotide under the control of a strong promoter system), and transgenic animals that express a NHP sequence, or "knock-outs" (which can be conditional) that do not express a functional NHP. Knock-out mice can be produced in several ways, one of which involves the use of mouse embryonic stem cell ("ES cell") lines that contain gene trap mutations in a murine homolog of at least one of the described NHPS. When the unique NHP sequences described in SEQ ID NOS:1–9 are "knocked-out" they provide a method of identifying phenotypic expression of the particular gene, as well as a method of assigning function to previously unknown genes. In addition, animals in which the unique NHP sequences described in SEQ ID NOS:1–9 are "knocked-out" provide an unique source in which to elicit antibodies to homologous and orthologous proteins, which would have been previously viewed by the immune system as "self" and therefore would have failed to elicit significant antibody responses.

To these ends, gene trapped knockout ES cells have been generated in murine homologs of the described NHPs. Characterization of mice in which both copies of a NHP have been disrupted (homozygotes) has allowed the identification of a novel role for this enzyme, and a model for the study of certain disorders. In particular, NHP knockout mice (that are homozygous for the mutated gene) display, intra alia, increased white blood cell counts. This suggests that these mice can be used as models for the study of the treatment of a variety of human conditions, including, but not limited to, neutropenia, as exemplified by neutropenia associated with the administration of myelosuppressive anti-cancer drugs.

In addition, the invention includes animals containing at least a single disrupted NHP allele (e.g., "knock-out" mice) that do not express normal levels of a NHP, humanized "knock-in" animals where the endogenous murine NHP gene has been replaced by one or more polynucleotides encoding at least a first human NHP protein, or animals harboring one or more NHP transgene (e.g., mice overexpressing a NHP). These animals may either transiently, inducibly, or constitutively express a NHP.

Additionally, the unique NHP sequences described in SEQ ID NOS:1–9 are useful for the identification of protein coding sequences, and mapping an unique gene to a particular chromosome. These sequences identify biologically verified exon splice junctions, as opposed to splice junctions that may have been bioinformatically predicted from genomic sequence alone. The sequences of the present invention are also useful as additional DNA markers for restriction fragment length polymorphism (RFLP) analysis, and in forensic biology, particularly given the presence of nucleotide polymorphisms within the described sequences.

Further, the present invention also relates to processes for identifying compounds that modulate, i.e., act as agonists or antagonists of, NHP expression and/or NHP activity that utilize purified preparations of the described NHPs and/or NHP products, or cells expressing the same. Such compounds can be used as therapeutic agents for the treatment of any of a wide variety of symptoms associated with biological disorders or imbalances, such as reduced white blood cell count.

The present invention also provides novel methods and compositions that can be used to facilitate drug discovery, drug development, and/or as treatments of conditions such as reduced white blood cell count, and the complications resulting therefrom. The present invention is based on the identification and novel functional characterization of the NHPs described herein.

The invention encompasses diagnostic assays that make use of the NHP polynucleotide sequences, or portions thereof, host cells expressing such nucleotides, and the expression products of such nucleotides, nucleotides that encode mammalian versions of the NHPs, including human NHPs, nucleotides that encode NHP mutants and the corresponding mutant NHP expression products, nucleotides that encode portions of a NHP that correspond to one or more of the NHP functional domains and the polypeptide products specified by such nucleotide sequences, and nucleotides that encode fusion proteins containing a NHP or one or more of its domains fused to another polypeptide.

The present invention also features assays for the identification of compounds that modulate NHP activity in the body. Such compounds can be used as agents to affect NHP-mediated processes, for example, as therapeutic agents for the treatment of low white blood cell count. The present invention also contemplates methods of using mammalian NHP protein(s), and particularly recombinantly expressed human NHP protein(s), in cell-free and/or cell-based assays for identifying compounds (modulators) that bind to and/or antagonize or otherwise modulate (i.e., increase or decrease) NHP activity. Compounds developed using such assays are then typically used in in vivo assays to determine the effect of such compounds on NHP-mediated processes, and to discern or verify the observed phenotypic effects. Such phenotypic effects include, but are not limited to, increased white blood cell count or reduction in one or more of the complications associated with reduced white blood cell count. The invention thus additionally contemplates compounds that bind to and/or activate or inhibit the activity of a NHP, as well as pharmaceutical compositions comprising such compounds, and the use of such compounds to treat NHP-related disorders.

In addition to small molecule agonists and antagonists of the NHPs, the invention also contemplates the use of large molecules to effect the levels or bioavailability of a NHP in vivo, including, but not limited to, mutant NHP proteins that compete with native NHPs, anti-NHP antibodies, anti-idiotypic antibodies that bind anti-NHP antibodies or NHP binding partners, nucleotide sequences that can be used to inhibit NHP expression (e.g., antisense, ribozyme and/or triplex molecules, and coding sequence or regulatory sequence replacement constructs) or to enhance NHP expression (e.g., expression constructs that place a NHP sequence under the control of a strong promoter or expression system).

In addition, the invention encompasses methods and compositions for the diagnostic evaluation, typing and prognosis of NHP-mediated disorders, including, inter alia, low white blood cell count, and for the identification of subjects having a predisposition to such conditions.

For example, in another embodiment of the present invention, NHP nucleic acid molecules of the invention can be used as diagnostic hybridization probes or as primers for diagnostic PCR analysis for the identification of NHP gene mutations, allelic variations, and/or regulatory defects in a NHP gene. NHP sequences may be used in hybridization or amplification assays of biological samples to detect abnormalities involving NHP gene structure, including point mutations, insertions, deletions and/or chromosomal rearrangements. Such diagnostic assays include, but are not limited to, Southern analyses, single stranded conformational polymorphism analyses (SSCP), restriction fragment length polymorphisms (RFLP), coding single nucleotide polymorphisms (cSNP) and PCR analyses. These assays can be combined with "gene chip" technology and used to screen pre-existing genetic databases of patients suffering from various NHP-mediated disorders. The sequences of the present invention are also useful as additional DNA markers for forensic biology. The present invention further provides for diagnostic kits for practicing such methods.

4.0 DESCRIPTION OF THE SEQUENCE LISTING AND FIGURES

The Sequence Listing provides the sequences of 4 calpain-like ORFs that encode the described NHP amino acid sequences.

5.0 DETAILED DESCRIPTION OF THE INVENTION

The NHPs, described for the first time herein, are novel proteins that are expressed in, inter alia, human cell lines, and human prostate and testis cells. The described sequences were compiled from gene trapped cDNAs and clones isolated from a human testis cDNA library (Edge Biosystems, Gaithersburg, Md.).

The present invention encompasses the nucleotides presented in the Sequence Listing, host cells expressing such nucleotides, the expression products of such nucleotides, and: (a) nucleotides that encode mammalian homologs of the described polynucleotides, including the specifically described NHPs, and the NHP products; (b) nucleotides that encode one or more portions of the NHPs that correspond to functional domains, and the polypeptide products specified by such nucleotide sequences, including, but not limited to, the novel regions of any active domain(s); (c) isolated nucleotides that encode mutant versions, engineered or naturally occurring, of the described NHPs, in which all or a part of at least one domain is deleted or altered, and the polypeptide products specified by such nucleotide sequences, including, but not limited to, soluble proteins and peptides; (d) nucleotides that encode chimeric fusion proteins containing all or a portion of a coding region of a NHP, or one of its domains (e.g., a receptor binding domain, accessory protein/self-association domain, etc.) fused to another peptide or polypeptide; or (e) therapeutic or diagnostic derivatives of the described polynucleotides, such as oligonucleotides, antisense polynucleotides, ribozymes, dsRNA, or gene therapy constructs comprising a sequence first disclosed in the Sequence Listing.

The present invention also includes murine NHPs, mutated murine embryonic stem cell clones, and animals derived from these embryonic stem cells. Characterization of mice in which NHP gene function has been disrupted (knock-outs) indicates that the NHPs play a role in conditions including, but not limited to, reduced white blood cell count, one or more of the complications arising from reduced white blood cell count, and other disorders, as detailed herein.

The invention encompasses the use of NHP nucleotides, NHP proteins and peptides, as well as antibodies to NHPs (that can, for example, act as NHP agonists or antagonists), antagonists (peptides, small organic molecules, fusion proteins, etc.) that inhibit NHP activity or expression, or agonists that activate NHP activity or increase its expression, in the identification, diagnosis, prognosis, and/or treatment of NHP-mediated disorders. The diagnosis of a NHP abnormality in a patient, or an abnormality in a NHP regulatory pathway, can also facilitate the development of treatments or therapeutic regimens. In addition, NHP nucleotides and NHP proteins can be used to identify compounds effective in the treatment of, among other things, NHP-mediated disorders, including, but not limited to, reduced white blood cell count. In addition, the present invention encompasses methods and compositions for the diagnostic evaluation, typing and prognosis of NHP-mediated disorders including, but not limited to, reduced white blood cell count.

An additional embodiment of the present invention relates to methods of using NHP polynucleotides and/or NHP gene products (proteins, polypeptides and/or peptides) for the identification of compounds that modulate, i.e., act as agonists or antagonists, of NHP gene expression and/or NHP gene product activity. Such compounds can be used as agents to manipulate NHP-mediated disorders and, in particular, as therapeutic agents for the treatment of NHP-mediated disorders. Such methods and compositions are typically capable of modulating the level of NHP gene expression and/or the level of NHP gene product activity. The basis for these aspects of the present invention is the novel discovery that the elimination of both NHP alleles results in, among other effects, increased white blood cell counts, as shown herein below.

The invention described in the subsections below thus encompasses NHP polypeptides or peptides corresponding to one or more of the functional domains of a NHP, mutated, truncated or deleted NHPs, NHP fusion proteins (e.g., a NHP or one or more functional domains of a NHP fused to an unrelated protein or peptide, such as albumin or an immunoglobulin constant region, i.e., IgFc), nucleotide sequences encoding such products, and host cell expression systems that can produce such NHP products.

The invention also encompasses antibodies and anti-idiotypic antibodies, or fragments thereof (including Fab and F(ab')$_2$ fragments), antagonists and agonists of a NHP, as well as compounds or nucleotide constructs that inhibit expression of a NHP gene (transcription factor inhibitors, antisense and ribozyme molecules, and/or coding sequence or regulatory sequence replacement constructs), or promote expression or overexpression of a NHP (e.g., expression constructs in which NHP coding sequences are operatively associated with expression control elements, such as promoters, promoter/enhancers, etc.).

The NHP proteins, polypeptides or peptides, NHP fusion proteins, NHP nucleotide sequences, antibodies, antagonists and/or agonists can be useful for the detection of mutant NHPs or inappropriately expressed NHPS, which can be used, for example, to diagnose NHP-mediated disorders. The NHP proteins or peptides, NHP fusion proteins, NHP nucleotide sequences, host cell expression systems, antibodies, antagonists, agonists and genetically engineered cells and animals can also be used for screening for drugs (or high throughput screening of combinatorial libraries) effective in the treatment of the symptomatic or phenotypic manifestations of perturbing the normal function of a NHP in the body. The use of engineered host cells and/or animals can offer an advantage in that such systems allow not only for the identification of compounds that bind to the endogenous receptor/ligand of a NHP, but can also identify compounds that trigger NHP-mediated activities or pathways.

Where, as in the present instance, some of the described NHP peptides or polypeptides are thought to be cytoplasmic or nuclear proteins, expression systems can be engineered that produce soluble derivatives of a NHP (such as those corresponding to NHP extracellular and/or intracellular domains, or truncated NHP polypeptides lacking one or more hydrophobic domains) and/or NHP fusion protein products (especially NHP-Ig fusion proteins, i.e., fusions of one or more NHP domain(s) to an IgFc). These expression products, as well as NHP antibodies, anti-idiotypic antibodies (including Fab fragments), and NHP antagonists or agonists (including compounds that modulate or act on downstream targets in a NHP-mediated pathway), can be used to directly treat diseases or disorders. For instance, the administration of an effective amount of soluble NHP, or a NHP-IgFc fusion protein or an anti-idiotypic antibody (or its Fab) that mimics a NHP could activate or effectively antagonize the endogenous NHP or a protein interactive therewith. Nucleotide constructs encoding such NHP products can be used to genetically engineer host cells to express such products in vivo; these genetically engineered cells function as "bioreactors" in the body, delivering a continuous supply of a NHP, a NHP peptide, or a NHP fusion protein to the body. Nucleotide constructs encoding functional NHPs, mutant NHPs, as well as antisense and ribozyme molecules, can also be used in "gene therapy" approaches for the modulation of NHP expression (and, consequently, modulating white blood cell counts higher or lower). Thus, the invention also encompasses pharmaceutical formulations and methods for treating biological disorders.

Various aspects of the invention are described in greater detail in the subsections below.

5.1 The NHP Nucleotide Sequences

The cDNA sequences (SEQ ID NOS:1, 3, 5, 7, and 9) and the corresponding deduced amino acid sequences (SEQ ID NOS:2, 4, 6, and 8) of the described NHPs are presented in the Sequence Listing. The NHP genes were obtained from a human testis cDNA library using probes and/or primers generated from human gene trapped sequence tags. Expression analysis has provided evidence that the described NHPs can be expressed, for example, in human testis, prostate, and gene trapped human cells. In addition to human calpain genes, the described NHPs share significant similarity to a variety of proteases from mice, pigs, chickens, and rats.

The described open reading frames can also contain several polymorphisms, including: an A to G transition corresponding to, for example, base 1474 of SEQ ID NOS:1 or 3, which can result in either a K or an E being present at the corresponding amino acid position of SEQ ID NOS:2 or 4; a C to T transition corresponding to, for example, base 1669 of SEQ ID NOS:1 or 3, which can result in a Q or a stop codon that truncates the ORF at the corresponding amino acid position of SEQ ID NOS:2 or 4; and a T to A transversion corresponding to, for example, base 1673 of SEQ ID NOS:1 or 3, which can result in a L or a H at the corresponding amino acid position of SEQ ID NOS:2 or 4.

As discussed above, the present invention includes the human DNA sequences presented in the Sequence Listing (and vectors comprising the same), and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel et al., eds., 1989, Current Protocols in Molecular Biology, Vol. I, Green Publishing Associates, Inc., and John Wiley & Sons, Inc., N.Y., at p. 2.10.3) and encodes a functionally equivalent expression product. Additionally contemplated are any nucleotide sequences that hybridize to the complement of a DNA sequence that encodes and expresses an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include, but are not limited to, naturally occurring NHPs present in other species, and mutant NHPS, whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar to corresponding regions of, for example, SEQ ID NO:1 (as measured by BLAST sequence comparison analysis using, for example, the University of Wisconsin GCG sequence analysis package (SEQUENCHER 3.0, Gene Codes Corp., Ann Arbor, Mich.) using default parameters).

The invention also includes nucleic acid molecules, preferably DNA molecules, that hybridize to, and are therefore the complements of, the described NHP-encoding polynucleotides. Such hybridization conditions can be highly stringent or less highly stringent, as described herein. In instances where the nucleic acid molecules are deoxyoligonucleotides ("DNA oligos"), such molecules are generally about 16 to about 100 bases long, or about 20 to about 80 bases long, or about 34 to about 45 bases long, or any variation or combination of sizes represented therein that incorporate a contiguous region of sequence first disclosed in the Sequence Listing.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific NHP oligonucleotide sequence(s) first disclosed in SEQ ID NOS:1–9. Alternatively, a restriction map specifying the relative positions of restriction endonuclease digestion sites, or various palindromic or other specific oligonucleotide sequences, can be used to structurally describe a given sequence. Such restriction maps, which are typically generated by widely available computer programs (e.g., the University of Wisconsin GCG sequence analysis package, etc.), can optionally be used in conjunction with one or more discrete nucleotide sequence(s) present in the sequence that can be described by the relative position of the sequence relative to one or more additional sequence(s), or one or more restriction sites, present in the disclosed sequence.

These nucleic acid molecules may encode or act as NHP antisense molecules, useful, for example, in NHP gene regulation and/or as antisense primers in amplification reactions of NHP nucleic acid sequences. With respect to NHP gene regulation, such techniques can be used to regulate one or more of the biological functions associated with a NHP, as described herein. Further, such sequences can be used as part of ribozyme and/or triple helix sequences that are also useful for NHP gene regulation.

Inhibitory antisense or double stranded oligonucleotides can additionally comprise at least one modified base moiety that is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

The antisense oligonucleotides can also comprise at least one modified sugar moiety selected from the group including, but not limited to, arabinose, 2-fluoroarabinose, xylulose, and hexose.

In yet another embodiment, the antisense oligonucleotides will comprise at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotides are α-anomeric oligonucleotides. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide can also be a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a NHP.

Further, NHP homologs and orthologs can be isolated from nucleic acids from additional mammalian species, for example, by performing PCR using two degenerate or "wobble" oligonucleotide primer pools designed on the basis of amino acid sequences within the NHP sequences disclosed herein. The template for the reaction may be genomic DNA, or total RNA, mRNA, and/or cDNA obtained by reverse transcription of mRNA prepared from, for example, human or non-human cell lines, cell types, or tissues known to express, or suspected of expressing, an allele of a NHP gene.

The PCR product can be sequenced directly, or subcloned and sequenced, to ensure that the amplified sequences represent NHP coding sequences. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known to express, or suspected of expressing, a NHP). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see, e.g., Sambrook et al., 1989, Molecular Cloning, A Laboratory Manual, Cold Spring Harbor Press, N.Y. (and periodic updates thereof).

NHP sequences can also be used to isolate mutant alleles of a NHP. Such mutant alleles can be isolated from individuals either known to have, or suspected of having, a genotype that contributes to increased white blood cell counts. Mutant alleles and/or peptides, polypeptides or proteins may then be utilized in the therapeutic and diagnostic programs described herein. Additionally, such sequences of any of the genes corresponding to NHPs can be used to detect gene regulatory (e.g., promoter or promoter/enhancer) defects that can affect, for example, white blood cell counts.

A cDNA encoding a mutant NHP gene or sequence can be isolated, for example, by using PCR. In this case, the first cDNA strand may be synthesized by hybridizing an oligo-dT oligonucleotide to mRNA isolated from tissue known to express or suspected of expressing a mutant NHP gene in an individual putatively carrying a mutant NHP allele, and by extending the new strand with reverse transcriptase. The second strand of the cDNA is then synthesized using an oligonucleotide that hybridizes specifically to the 5' end of the normal NHP gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of carrying, or known to carry, a mutant NHP allele (e.g., a person manifesting a NHP-associated phenotype such as, for example, increased white blood cell counts), or a cDNA library can be constructed using RNA from a tissue known to express, or suspected of expressing, a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known to express, or suspected of expressing, a mutant NHP allele in an individual suspected of carrying, or known to carry, such a mutant allele. In this manner, gene products made by the putatively mutant tissue may be expressed and screened using standard antibody screening techniques in conjunction with antibodies raised against a normal NHP product, as described below (for screening techniques, see, for example, Harlow and Lane, eds., 1988, "Antibodies: A Laboratory Manual", Cold Spring Harbor Press, Cold Spring Harbor, N.Y., incorporated herein by reference in its entirety).

Additionally, screening can be accomplished by screening with labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to a NHP are likely to cross-react with a corresponding mutant NHP gene product. Library clones detected via their reaction with such labeled antibodies can be purified and subjected to sequence analysis according to methods well known in the art.

The invention also encompasses nucleotide sequences that encode mutant isoforms of any of the NHP amino acid sequences, peptide fragments thereof, truncated versions thereof, and/or fusion proteins, including any of the above fused to another unrelated polypeptide. Examples of such polypeptides can include, but are not limited to, an epitope tag that aids in purification or detection of the resulting fusion protein, or an enzyme, fluorescent protein, or luminescent protein that can be used as a marker.

The present invention additionally encompasses: (a) RNA or DNA vectors that contain any portion of a NHP and/or its complement, as well as any of the peptides or proteins encoded thereby; (b) DNA vectors that contain a cDNA that substantially spans the entire open reading frame corresponding to any of the NHP sequences and/or their complements; (c) DNA expression vectors that contain any of the foregoing sequences, or a portion thereof, operatively associated with a regulatory element that directs the expression of the coding sequences in the host cell; and (d) genetically engineered host cells that contain a cDNA that spans the entire open reading frame, or any portion thereof, corresponding to any of the NHP sequences, operatively associated with a regulatory element, which may be exogenously controlled (such as in gene activation), either in vivo and/or in vitro, which directs the expression of NHP coding sequences in the host cell.

As used herein, regulatory elements include, but are not limited to, inducible and non-inducible promoters, enhancers, operators, and other elements known to those skilled in the art that drive and regulate expression. Such regulatory elements include, but are not limited to, the baculovirus polyhedrin promoter, the cytomegalovirus (hCMV) immediate early gene promoter, regulatable, viral elements (particularly retroviral LTR promoters), the early or late promoters of SV40 and adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses nucleotide constructs encoding NHP products that can be used to genetically engineer host cells to express such NHP products in vivo. These genetically engineered cells function as "bioreactors" in the body, delivering a continuous supply of a NHP, NHP peptides or polypeptides, soluble NHPs, or NHP fusion proteins. Nucleotide constructs encoding functional versions of a NHP, mutant versions of a NHP, as well as antisense and ribozyme molecules, can be used in "gene therapy" approaches for the modulation of NHP expression and/or activity in the treatment of NHP-mediated disorders. Thus, the invention also encompasses pharmaceutical formulations and methods for treating NHP-mediated disorders such as reduced white blood cell count.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458, which are herein incorporated by reference in their entirety.

5.1.1 Cells that Contain NHP Disrupted Alleles

Another aspect of the current invention includes cells that contain a disrupted NHP gene. There are a variety of techniques that can be used to disrupt genes in cells, and especially ES cells. Examples of such methods are described in co-pending U.S. patent application Ser. No. 08/728,963, and U.S. Pat. Nos. 5,789,215, 5,487,992, 5,627,059, 5,631,153, 6,087,555, 6,136,566, 6,139,833, and 6,207,371, all of which are herein incorporated by reference in their entirety.

5.1.2 Identification of Cells that Express a NHP

Host cells that contain NHP coding sequence and/or express a biologically active NHP gene product, or fragment thereof, can be identified by at least four general approaches: (a) DNA-DNA or DNA-RNA hybridization; (b) the presence or absence of "marker" gene functions; (c) assessing the level of NHP transcription as measured by the expression of NHP mRNA transcripts in the host cell; and (d) detection of NHP gene product as measured by immunoassay, enzymatic assay, chemical assay, or one or more of the biological activities of NHPs. These identification methods are described in greater detail below. Prior to screening for gene expression, the host cells can first be treated in an effort to increase the level of expression of sequences encoding NHP polynucleotides, especially in cell lines that produce low amounts of NHP mRNAs and/or NHP peptides and proteins.

In approach (a) above, the presence of a NHP coding sequence can be detected by DNA-DNA or DNA-RNA hybridization using probes comprising nucleotide sequences that are homologous or complementary to the NHP coding sequences, as described herein, or portions or derivatives thereof.

In approach (b), the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if a NHP polynucleotide sequence that encodes a NHP peptide or protein is inserted within a marker gene sequence of a vector, recombinants containing a NHP coding sequence can be identified by the absence of marker gene function. Alternatively, a marker gene can be placed in tandem with a NHP sequence, under the control of the same or a different promoter used to control the expression of the NHP coding sequence. Expression of the marker gene product in response to induction or selection indicates the presence of the NHP coding sequence.

In approach (c), transcriptional activity of a coding region of a NHP can be assessed by hybridization assays. For example, RNA can be isolated and analyzed by Northern blot using a probe derived from a NHP, or any portion thereof. Alternatively, total nucleic acids of the host cell may be extracted and assayed for hybridization to such probes. Additionally, RT-PCR (using NHP specific oligos) may be used to detect low levels of gene expression in a sample, or in RNA isolated from a spectrum of different tissues, or in cDNA libraries derived from different tissues, to determine which tissues express a given NHP.

In approach (d), the expression of the peptides and proteins of the current invention can be assessed immunologically, for example by Western blots, immunoassays such as radioimmuno-precipitation, radioimmunoassays, enzyme-linked immunosorbent assays, and the like. This can be achieved by using an antibody, or a binding partner, specific to a NHP peptide or protein. Additionally, expression can be assessed by monitoring one or more of the biological activities of a NHP. The NHPs have, among others activities, activity as a protease, and is therefore involved in protein degradation. Thus assays described herein, as well as those commonly known to those of skill in the art to examine proteases, can be used to access NHP biological activity.

5.1.3 The Use of NHP Polynucleotide Sequences to Diagnose NHP-Mediated Disorders The NHP polynucleotide sequences, as described herein, can be used in hybridization based assays to identify and diagnose NHP-mediated disorders that result from mutant NHP sequences, or to quantify levels of NHP expression, thus identifying individuals that are at risk for developing NHP-mediated disorders. These assays could be in the form of fluorescence or enzyme based in situ hybridization, PCR, or in a preferred embodiment, hybridization probes used to assess gene expression patterns using a microarray or high-throughput "chip" format.

The present invention includes assays that utilize, among others, NHP sequences (and vectors comprising the same), a open reading frame (ORF) encoding a naturally occurring protein having NHP activity and that hybridizes to a complement of a NHP DNA sequence under highly stringent conditions, as described herein, and encodes a functionally equivalent gene product, as described herein. The present assays also contemplate the use of any nucleotide sequences that hybridize to the complement of a nucleotide sequence that encodes a NHP under moderately stringent conditions, as described herein, yet still encodes a functionally equivalent NHP product, as described herein.

The invention also includes the use of nucleic acid molecules, preferably DNA molecules, that hybridize to, and are therefore the complements of, the described NHP nucleotide sequences. Such hybridization conditions may be highly stringent or less highly stringent, as described herein. In instances where the nucleic acid molecules are "DNA oligos", such molecules are generally about 16 to about 100 bases long, or about 20 to about 80 bases long, or about 34 to about 45 bases long, or any variation or combination of sizes represented therein that incorporate a contiguous region of NHP sequence. Such oligonucleotides can be used, for example, in conjunction with the polymerase chain reaction (PCR) to screen libraries, isolate clones, and prepare cloning and sequencing templates, etc.

For oligonucleotide probes, highly stringent conditions can typically refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). Oligonucleotides of the invention can be synthesized by standard methods known in the art, e.g., by use of an automated DNA synthesizer (such as are commercially available from Biosearch, Applied Biosystems, etc.).

As examples, phosphorothioate oligonucleotides can be synthesized (Stein et al., 1988, Nucl. Acids Res. 16:3209), and methylphosphonate oligonucleotides can be prepared by use of controlled pore glass polymer supports (Sarin et al., 1988, Proc. Natl. Acad. Sci. USA 85:7448–7451), etc.

Low stringency conditions are well-known to those of skill in the art, and will vary predictably depending on the specific organisms from which the library and the labeled sequences are derived. For guidance regarding such conditions, see, for example, Sambrook, et al., 1989, supra, and Ausubel, et al., 1989, supra (and periodic updates of both).

Alternatively, NHP oligonucleotides and/or amino acids can be used as hybridization probes for screening libraries, or assessing gene expression patterns (particularly using a microarray or high-throughput "chip" format). Such assays would be applicable to the screening of large databases containing, for example, sequences obtained from patients suspected of having a NHP defect. This methodology would therefore link functional information with large amounts of genetic information.

Additionally, a series of NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS:1–9 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS:1–9, or an amino acid sequence encoded thereby. Methods for attaching biopolymers to, or synthesizing biopolymers on, solid support matrices, and conducting binding studies thereon, are disclosed in, inter alia, U.S. Pat. Nos. 5,700,637, 5,556,752, 5,744,305, 4,631,211, 5,445,934, 5,252,743, 4,713,326, 5,424,186, and 4,689,405, the disclosures of which are herein incorporated by reference in their entirety.

Addressable arrays comprising sequences first disclosed in SEQ ID NOS:1–9 can be used to identify and characterize the temporal and tissue specific expression of a gene. These addressable arrays incorporate oligonucleotide sequences of sufficient length to confer the required specificity, yet be within the limitations of the production technology. The length of these probes is usually within a range of between about 8 to about 2000 nucleotides. Preferably the probes consist of 60 nucleotides, and more preferably 25 nucleotides, from the sequences first disclosed in SEQ ID NOS:1–9.

For example, a series of NHP oligonucleotide sequences, or the complements thereof, can be used in chip format to represent all or a portion of the described NHP sequences. The oligonucleotides, typically between about 16 to about 40 (or any whole number within the stated range) nucleotides in length, can partially overlap each other, and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing, and proceed in either a sense (5'-to-3') orientation vis-a-vis the described sequence or in an antisense (3'-to-5') orientation.

Microarray-based analysis allows the discovery of broad patterns of genetic activity, providing new understanding of gene functions, and generating novel and unexpected insight into transcriptional processes and biological mechanisms. The use of addressable arrays comprising sequences first disclosed in SEQ ID NOS:1–9 provides detailed information about transcriptional changes involved in a specific pathway, potentially leading to the identification of novel components, or gene functions that manifest themselves as novel phenotypes.

Probes consisting of sequences first disclosed in SEQ ID NOS:1–9 can also be used in the identification, selection, and validation of novel molecular targets for drug discovery. The use of these unique sequences permits the direct confirmation of drug targets, and recognition of drug dependent changes in gene expression that are modulated through pathways distinct from the intended target of the drug. These unique sequences therefore also have utility in defining and monitoring both drug action and toxicity.

As an example of utility, the sequences first disclosed in SEQ ID NOS:1–9 can be utilized in microarrays, or other assay formats, to screen collections of genetic material from patients who have a particular medical condition. These investigations can also be carried out using the sequences first disclosed in SEQ ID NOS:1–9 in silico, and by comparing previously collected genetic databases and the disclosed sequences using computer software known to those in the art. Thus the sequences first disclosed in SEQ ID NOS:1–9 can be used to identify mutations associated with a particular disease, and also in diagnostic or prognostic assays.

In addition to the NHP nucleotide sequences described herein, additional full length NHP cDNA or gene sequences present in the same or similar species (such as, for example, additional splice variants, polymorphisms, pseudogenes, etc.), and/or homologs or orthologs of the NHP gene present in other species, can be identified and readily isolated by standard molecular biological techniques using the NHP sequences presented herein. The identification of homologs of a NHP in related species can be useful, for example, in developing alternative animal model systems for the purpose of drug discovery.

Labeled NHP nucleotide probes can also be used to screen a genomic library derived from an organism of interest, again, using appropriately stringent conditions. In particular, the identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests and clinical protocols for treating NHP-related disorders in human patients. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in prognostics and/or diagnostics.

For example, the present sequences can be used in restriction fragment length polymorphism (RFLP) analysis to identify specific individuals. In this technique, an individual's genomic DNA is digested with one or more restriction enzymes, and probed on a Southern blot to yield unique bands for identification (as generally described in U.S. Pat. No. 5,272,057, incorporated herein by reference). In addition, the sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). Actual base sequence information can be used for identification as an accurate alternative to patterns formed by restriction enzyme generated fragments.

5.2 NHP Polypeptides

NHPs, NHP polypeptides, NHP peptide fragments, mutated, truncated, or deleted forms of the NHPs, and/or NHP fusion proteins can be prepared for a variety of uses. These uses include, but are not limited to, the generation of antibodies, as reagents in diagnostic assays, for the identification of other cellular gene products related to a NHP, and as reagents in assays for screening for compounds that can be used as pharmaceutical reagents useful in the therapeutic treatment of mental, biological, or medical disorders and diseases. Given the similarity information and expression data, the described NHPs can be targeted (by drugs, oligos, antibodies, etc.) in order to treat disease, or to augment the efficacy of therapeutic agents.

The Sequence Listing discloses the amino acid sequences encoded by the described NHP polynucleotide sequences. The NHPs have initiator methionines in DNA sequence contexts consistent with a translation initiation site. The sequence data presented herein indicate that alternatively spliced forms of the NHPs exist (which may or may not be tissue specific).

The NHP amino acid sequences of the invention include the nucleotide and amino acid sequences presented in the Sequence Listing, as well as analogues and derivatives thereof. Further, corresponding NHP homologues from other species are encompassed by the invention. In fact, any NHP protein encoded by the NHP nucleotide sequences described herein are within the scope of the invention, as are any novel polynucleotide sequences encoding all or any novel portion of an amino acid sequence presented in the Sequence Listing. The degenerate nature of the genetic code is well-known, and, accordingly, each amino acid presented in the Sequence Listing is generically representative of the well-known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al., eds., Scientific American Books, New York, N.Y., herein incorporated by reference), are generically representative of all the various permutations and combinations of nucleic acid sequences that can encode such amino acid sequences.

The invention also encompasses proteins that are functionally equivalent to the NHPs encoded by the presently described nucleotide sequences, as judged by any of a number of criteria, including, but not limited to, the ability to bind and cleave a substrate of a NHP, or the ability to effect an identical or complementary downstream signal transduction pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described herein, but that result in a silent change, thus producing a functionally equivalent expression product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

While random mutations can be made to NHP DNA (using random mutagenesis techniques well-known in the art), and the resulting NHP mutants tested for activity, site-directed mutations of a NHP coding sequence can be engineered (using site-directed mutagenesis techniques well-known to those skilled in the art) to generate NHP mutants with increased or decreased function.

For example, the novel amino acid sequence of peptides, polypeptides and proteins encoded by a NHP can be aligned with homologs from different species. Mutant peptides, polypeptides and proteins can be engineered so that regions of interspecies identity are maintained, whereas the variable residues are altered, e.g., by deletion or insertion of an amino acid residue(s) or by substitution of one or more different amino acid residues. For example, alterations in variable residues may be designed to produce a mutant form of a NHP peptide, polypeptide or protein that is more stable but retains function. Other alterations may be designed to alter function, such as those designed to enhance binding or enzymatic activity of a NHP product. One of skill in the art could easily test such mutant or deleted forms of a NHP peptide, polypeptide or protein for the effect of such alterations on function using the teachings presented herein.

Other mutations to the coding sequences described herein can be made to generate peptides, polypeptides and proteins that are better suited for expression, scale up, etc., in the host cells chosen. For example, the triplet code for each amino acid can be modified to conform more closely to the preferential codon usage of the translational machinery of the particular host cell, or, for example, to yield a messenger RNA molecule with a longer half-life. Those skilled in the art would readily know what modifications of the nucleotide sequence would be desirable to conform the nucleotide sequence to preferential codon usage or to make the messenger RNA more stable. Such information would be obtainable, for example, through use of computer programs, through review of available research data on codon usage and messenger RNA stability, and through other means known to those of skill in the art.

Additionally contemplated are oligopeptides that are modeled on an amino acid sequence first described in the Sequence Listing. Such NHP oligopeptides are generally between about 10 to about 100 amino acids long, or between about 16 to about 80 amino acids long, or between about 20 to about 35 amino acids long, or any variation or combination of sizes represented therein that incorporate a contiguous region of sequence first disclosed in the Sequence Listing. Such NHP oligopeptides can be of any length disclosed within the above ranges and can initiate at any amino acid position represented in the Sequence Listing.

The invention also contemplates "substantially isolated" or "substantially pure" proteins or polypeptides. By a "substantially isolated" or "substantially pure" protein or polypeptide is meant a protein or polypeptide that has been separated from at least some of those components that naturally accompany it. Typically, the protein or polypeptide is substantially isolated or pure when it is at least 60%, by weight, free from the proteins and other naturally-occurring organic molecules with which it is naturally associated in vivo. Preferably, the purity of the preparation is at least 75%, more preferably at least 90%, and most preferably at least 99%, by weight. A substantially isolated or pure protein or polypeptide may be obtained, for example, by extraction from a natural source, by expression of a recombinant nucleic acid encoding the protein or polypeptide, or by chemically synthesizing the protein or polypeptide.

Purity can be measured by any appropriate method, e.g., column chromatography such as immunoaffinity chromatography using an antibody specific for the protein or polypeptide, polyacrylamide gel electrophoresis, or HPLC analysis. A protein or polypeptide is substantially free of naturally associated components when it is separated from at least some of those contaminants that accompany it in its natural state. Thus, a polypeptide that is chemically synthesized or produced in a cellular system different from the cell from which it naturally originates will be, by definition, substantially free from its naturally associated components. Accordingly, substantially isolated or pure proteins or polypeptides include eukaryotic proteins synthesized in *E. coli*, other prokaryotes, or any other organism in which they do not naturally occur.

5.2.1 NHP Fusion Proteins

Peptides corresponding to one or more portions of a NHP, truncated or deleted NHPS, as well as fusion proteins in which a full length NHP, a NHP peptide or truncated NHP is fused to an unrelated protein are also within the scope of the invention, and can be designed on the basis of NHP nucleotide and/or amino acid sequences disclosed herein. Such fusion proteins include, but are not limited to: IgFc fusions, which stabilize NHP proteins or peptides and prolong half-life in vivo; fusions to any amino acid sequence that allows the fusion protein to be anchored to the cell membrane; or fusions to an enzyme, fluorescent protein, or luminescent protein that provides a marker function.

Also encompassed by the present invention are fusion proteins that direct a NHP to a target organ and/or facilitate transport across the membrane into the cytosol. Conjugation of NHPs to antibody molecules, or their Fab or F(ab')$_2$ fragments, could be used to target cells bearing a particular epitope. Attaching an appropriate signal sequence to a NHP would also transport a NHP to a desired location within the cell. Alternatively targeting of a NHP or its nucleic acid sequence might be achieved using liposome or lipid complex based delivery systems. Such technologies are described in "Liposomes: A Practical Approach", New, R. R. C., ed., Oxford University Press, N.Y., and in U.S. Pat. Nos. 4,594,595, 5,459,127, 5,948,767 and 6,110,490 and their respective disclosures, which are herein incorporated by reference in their entirety. Additionally embodied are novel protein constructs engineered in such a way that they facilitate transport of NHPs to a target site or desired organ, where they cross the cell membrane and/or the nucleus where the NHPs can exert their functional activity. This goal may be achieved by coupling of a NHP to a cytokine or other ligand that provides targeting specificity, and/or to a protein transducing domain (see generally U.S. Provisional Patent Application Ser. Nos. 60/111,701 and 60/056,713, both of which are herein incorporated by reference, for examples of such transducing sequences), to facilitate passage across cellular membranes, and can optionally be engineered to include nuclear localization signals.

Alternatively, any fusion protein can be readily purified by utilizing an antibody specific for the fusion protein being expressed. Another exemplary system allows for the ready purification of non-denatured fusion proteins expressed in human cell lines (Janknecht et al., 1991, Proc. Natl. Acad. Sci. USA 88:8972–8976). In this system, the sequence of interest is subcloned into a vaccinia recombination plasmid such that the sequence's open reading frame is translationally fused to an amino-terminal tag consisting of six histidine residues. Extracts from cells infected with recombinant vaccinia virus are loaded onto $Ni^{2+}$.nitriloacetic acid-agarose columns, and histidine-tagged proteins are selectively eluted with imidazole-containing buffers.

The novel gene products/peptide sequences encoded by NHPs are also useful as epitope tags for antigenic or other tagging of proteins and polypeptides that have been engineered to incorporate or comprise at least a portion of a NHP peptide sequence.

5.2.2 NHP Expression Systems

While NHP polypeptides and peptides can be chemically synthesized (e.g., see Creighton, 1983, Proteins: Structures and Molecular Principles, W. H. Freeman & Co., N.Y.), large polypeptides derived from NHPs, and full length NHPs themselves, may advantageously be produced by recombinant DNA technology using techniques well-known in the art for expressing nucleic acids containing NHP gene sequences and/or coding sequences. Such methods can be used to construct expression vectors containing NHP nucleotide sequences and appropriate transcriptional and translational control signals. These methods include, for example, in vitro recombinant DNA techniques, synthetic techniques, and in vivo genetic recombination (see, for example, the techniques described in Sambrook et al., 1989, supra, and Ausubel et al., 1989, supra). Alternatively, RNA and/or DNA encoding NHP nucleotide sequences may be chemically synthesized using, for example, synthesizers (see, for example, the techniques described in "Oligonucleotide Synthesis", 1984, Gait, ed., IRL Press, Oxford, which is incorporated by reference herein in its entirety).

A variety of host-expression vector systems can be used to express the NHP nucleotide sequences of the invention. Where the NHP peptide or polypeptide is a soluble derivative of, for example, a membrane protein (e.g., NHP peptides derived from an extracellular domain (ECD) of a NHP, or truncated or deleted NHPs in which a transmembrane (TM) and/or cytoplasmic domain (CD) have been deleted, etc.) the peptide or polypeptide can be recovered from the culture, i.e., from the host cell in cases where the NHP peptide or polypeptide is not secreted, or from the culture media in cases where the NHP peptide or polypeptide is secreted by the cells. However, such expression systems also encompass engineered host cells that express a NHP, or functional equivalent, in situ, i.e., anchored in the cell membrane. Purification or enrichment of a NHP from such expression systems can be accomplished using appropriate detergents and lipid micelles and methods well-known to those skilled in the art. However, such engineered host cells themselves may be used in situations where it is important not only to retain the structural and functional characteristics of a NHP, but to assess biological activity, e.g., in certain drug screening assays.

For long-term, high-yield production of recombinant proteins, stable expression is preferred. For example, cell lines that stably express the NHP sequences described herein may be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then switched to a selective media. The selectable marker in the recombinant plasmid confers resistance to the selection and allows cells to stably integrate the plasmid into their chromosomes and grow to form foci, which in turn can be cloned and expanded into cell lines. This method may advantageously be used to engineer cell lines that express the NHP product. Such engineered cell lines may be particularly useful in screening and evaluation of compounds that affect the endogenous activity of the NHP product.

A number of selection systems may be used, including, but not limited to, the herpes simplex virus thymidine kinase (Wigler et al., 1977, Cell 11:223), hypoxanthine-guanine phosphoribosyltransferase (Szybalska and Szybalski, 1962, Proc. Natl. Acad. Sci. USA 48:2026), and adenine phosphoribosyltransferase (Lowy et al., 1980, Cell 22:817) genes, which can be employed in $tk^-$, $hgprt^-$ or $aprt^-$ cells, respectively. Also, antimetabolite resistance can be used as the basis of selection for the following genes: dhfr, which confers resistance to methotrexate (Wigler et al., 1980, Proc. Natl. Acad. Sci. USA 77:3567; O'Hare et al., 1981, Proc. Natl. Acad. Sci. USA 78:1527); gpt, which confers resistance to mycophenolic acid (Mulligan and Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147).

The expression systems that may be used for purposes of the invention include, but are not limited to, microorganisms such as bacteria (e.g., *E. coli*, *B. subtilis*) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP nucleotide sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing NHP nucleotide sequences and promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing a NHP, or for raising antibodies to a NHP, vectors that direct the expression of high levels of fusion protein products that are readily purified may be desirable. Such vectors include, but are not limited to, the *E. coli* expression vector pUR278 (Ruther et al., 1983, EMBO J. 2:1791), in which a NHP coding sequence may be ligated individually into the vector in-frame with the lacZ coding region so that a fusion protein is produced; pIN vectors (Inouye and Inouye, 1985, Nucleic Acids Res. 13:3101–3109; Van Heeke and Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target expression product can be released from the GST moiety.

In an exemplary insect system, *Autographa californica* nuclear polyhedrosis virus (AcNPV) is used as a vector to phosphoribosyltransferase (Szybalska and Szybalski, 1962, Proc. Natl. Acad. Sci. USA 48:2026), and adenine phosphoribosyltransferase (Lowy et al., 1980, Cell 22:817) genes, which can be employed in $tk^-$, $hgprt^-$ or $aprt^-$ cells, respectively. Also, antimetabolite resistance can be used as the basis of selection for the following genes: dhfr, which confers resistance to methotrexate (Wigler et al., 1980, Proc. Natl. Acad. Sci. USA 77:3567; O'Hare et al., 1981, Proc. Natl. Acad. Sci. USA 78:1527); gpt, which confers resistance to mycophenolic acid (Mulligan and Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147).

The expression systems that may be used for purposes of the invention include, but are not limited to, microorganisms such as bacteria (e.g., *E. coli*, *B. subtilis*) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP nucleotide sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing NHP nucleotide sequences and promoters derived from the genome of mammalian cells (e.g., metallothionein promoter) or from mammalian viruses (e.g., the adenovirus late promoter; the vaccinia virus 7.5K promoter). translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., 1987, Methods in Enzymol. 153:516–544).

In yeast, a number of vectors containing constitutive or inducible promoters may be used. For a review, see Ausubel et al., 1989, supra, Ch. 13; Grant et al., 1987, Methods in Enzymol. 153:516–544; Glover, 1986, DNA Cloning, Vol. II, IRL Press, Wash., D.C., Ch. 3; Bitter, 1987, Methods in Enzymol. 152:673–684; and Strathern et al., eds., "The Molecular Biology of the Yeast Saccharomyces", 1982, Cold Spring Harbor Press, Vols. I and II.

In cases where plant expression vectors are used, expression of a NHP coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559-565) may be used. These constructs can be introduced into plant cells using Ti plasmids, Ri plasmids, plant virus vectors, direct DNA transformation, microinjection, electroporation, etc. For reviews of such techniques, see, for example, Weissbach and Weissbach, 1988, Methods for Plant Molecular Biology, Academic Press, NY, Section VIII, pp. 421–463; and Grierson and Corey, 1988, Plant Molecular Biology, 2d Ed., Blackie, London, Ch. 7–9.

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct or desired modification and processing of the NHP protein, polypeptide or peptide expressed. To this end, eukaryotic host cells that possess the cellular machinery for proper processing of the primary transcript, glycosylation, and phosphorylation of the NHP gene product may be used. Such mammalian host cells include, but are not limited to, CHO, VERO, BHK, HeLa, COS, MDCK, 293, 3T3, WI38 and U937 cells, and in particular human cell lines.

5.2.3 NHP Transgenic Animals

The present invention provides for transgenic animals that carry a NHP transgene in all their cells, as well as animals that carry a NHP transgene in some, but not all their cells, i.e., mosaic animals or somatic cell transgenic animals. Animals of any species, including, but not limited to, mice, rats, rabbits, guinea pigs, pigs, micro-pigs, goats, and non-human primates, e.g., baboons, monkeys, and chimpanzees, can be used to generate transgenic animals carrying NHP polynucleotides. NHP transgenes may be integrated as a single transgene or in concatamers, e.g., head-to-head tandems or head-to-tail tandems. The transgene may also be selectively introduced into and activated in a particular cell type by following, for example, the teaching of Lasko et al., 1992, Proc. Natl. Acad. Sci. USA 89:6232–6236. The regulatory sequences required for such a cell-type specific activation will depend upon the particular cell type of interest, and will be apparent to those of skill in the art.

When it is desired that a NHP transgene be integrated into the chromosomal site of the endogenous copy of the NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide sequence of the endogenous NHP gene (i.e., "knockout" animals). In this way, the expression of the endogenous NHP gene may also be eliminated by inserting non-functional sequences into the endogenous NHP gene. The transgene may also be selectively introduced into a particular cell type, thus inactivating the endogenous NHP gene in only that cell type, by following, for example, the teaching of Gu et al., 1994, Science 265:103–106. The regulatory sequences required for such a cell-type specific inactivation will depend upon the particular cell type of interest.

Any technique known in the art may be used to introduce a NHP transgene into animals to produce the founder lines of transgenic animals. Such techniques include, but are not limited to, pronuclear microinjection (U.S. Pat. No. 4,873, 191, incorporated herein by reference); retrovirus-mediated gene transfer into germ lines (Van der Putten et al., 1985, Proc. Natl. Acad. Sci. USA 82:6148–6152); gene targeting in embryonic stem cells (Thompson et al., 1989, Cell 56:313–321); electroporation of embryos (Lo, 1983, Mol Cell. Biol. 3:1803–1814); sperm-mediated gene transfer (Lavitrano et al., 1989, Cell 57:717–723); and positive-negative selection as described in U.S. Pat. No. 5,464,764, herein incorporated by reference. For a review of such techniques, see Gordon, 1989, Transgenic Animals, Intl. Rev. Cytol. 115:171–229, which is incorporated by reference herein in its entirety.

Once transgenic animals have been generated, the expression of the recombinant NHP gene may be assayed utilizing standard techniques. Initial screening may be accomplished by Southern blot analysis or PCR techniques to analyze animal tissues to assay whether integration of the NHP transgene has taken place. The level of mRNA expression of the NHP transgene in the tissues of the transgenic animals may also be assessed using techniques that include, but are not limited to, Northern blot analysis of cell type samples lines or host systems can be chosen to ensure the correct or desired modification and processing of the NHP protein, polypeptide or peptide expressed. To this end, eukaryotic host cells that possess the cellular machinery for proper processing of the primary transcript, glycosylation, and phosphorylation of the NHP gene product may be used. Such mammalian host cells include, but are not limited to, CHO, VERO, BHK, HeLa, COS, MDCK, 293, 3T3, WI38 and U937 cells, and in particular human cell lines.

5.2.3 NHP Transgenic Animals

The present invention provides for transgenic animals that carry a NHP transgene in all their cells, as well as animals that carry a NHP transgene in some, but not all their cells, i.e., mosaic animals or somatic cell transgenic animals. Animals of any species, including, but not limited to, mice, rats, rabbits, guinea pigs, pigs, micro-pigs, goats, and non-human primates, e.g., baboons, monkeys, and chimpanzees, can be used to generate transgenic animals carrying NHP polynucleotides. NHP transgenes may be integrated as a single transgene or in concatamers, e.g., head-to-head tandems or head-to-tail tandems. The transgene may also be selectively introduced into and activated in a particular cell type by following, for example, the teaching of Lasko et al., 1992, Proc. Natl. Acad. Sci. USA 89:6232–6236. The regulatory sequences required for such a cell-type specific activation will depend upon the particular cell type of interest, and will be apparent to those of skill in the art.

When it is desired that a NHP transgene be integrated into the chromosomal site of the endogenous copy of the NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide and/or activity of a NHP expression product. Additionally, such antibodies can be used in conjunction with gene therapy to, for example, evaluate normal and/or engineered NHP-expressing cells prior to their introduction into a patient. Such antibodies may additionally be used in methods for the inhibition of abnormal NHP activity. Thus, such antibodies may be utilized as a part of treatment methods.

For the production of antibodies, various host animals may be immunized by injection with a NHP, a NHP peptide (e.g., one corresponding to a functional domain of a NHP), a truncated NHP polypeptide (a NHP in which one or more domains have been deleted), functional equivalents of a NHP, or mutated variants of a NHP. Such host animals may include, but are not limited to, pigs, rabbits, mice, goats, and rats, to name but a few. Various adjuvants may be used to increase the immunological response, depending on the host species, including, but not limited to, Freund's adjuvant (complete and incomplete), mineral salts such as aluminum hydroxide or aluminum phosphate, chitosan, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and/or coupling with molecules such as keyhole limpet hemocyanin, tetanus toxoid, diphtheria toxoid, ovalbumin, cholera toxin, or fragments thereof. Polyclonal antibodies are heterogeneous populations of antibody molecules derived from the sera of the immunized animals.

Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class, including IgG, IgM, IgE, IgA, and IgD, and any subclass thereof. The hybridomas producing the mAbs of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci. USA 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,114,598, 6,075,181 and 5,877,397 and their respective disclosures, which are herein incorporated by reference in their entirety. Also encompassed by the present invention is the use of fully humanized monoclonal antibodies, as described in U.S. Pat. No. 6,150,584 and respective disclosures, which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP expression products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include, but are not limited to: $F(ab')_2$ fragments, which can be produced by pepsin digestion of an antibody molecule; and Fab fragments, which can be generated by reducing the disulfide bridges of $F(ab')_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well-known to those skilled in the art (see, e.g., Greenspan and Bona, 1993, FASEB J. 7:437–444; and Nissinoff, 1991, J. Immunol. 147:2429–2438). For example, antibodies that bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or fragments of such anti-idiotypes can be used in therapeutic regimens involving a NHP signaling pathway.

Additionally given the high degree of relatedness of mammalian NHPs, the presently described knock-out mice (having never seen a NHP, and thus never been tolerized to a NHP) have an unique utility, as they can be advantageously applied to the generation of antibodies against the disclosed mammalian NHPs (i.e., a NHP will be immunogenic in NHP knock-out animals).

5.4 Diagnosis of NHP-Mediated Disorders

A variety of methods can be employed for the diagnostic and prognostic evaluation of NHP-mediated disorders. These methods can also be used to identify subjects having a predisposition to such disorders. Such methods may, for example, utilize reagents such as NHP nucleotide sequences, NHP proteins or peptides, and/or anti-NHP antibodies. Specifically, such reagents may be used, for example, for: (1) the detection of the presence of NHP gene mutations, or the detection of either over- or under-expression of a NHP mRNA relative to the non-NHP disorder state; (2) the detection of either an over- or an under-abundance of a NHP gene product Nature 256:495–497; and U.S. Pat. No. 4,376,110), the human B-cell hybridoma technique (Kosbor et al., 1983, Immunology Today 4:72; Cote et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class, including IgG, IgM, IgE, IgA, and IgD, and any subclass thereof. The hybridomas producing the mAbs of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci. USA 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,114,598, 6,075,181 and 5,877,397 and their respective disclosures, which are herein incorporated by reference in their entirety. Also encompassed by the present invention is the use of fully humanized monoclonal antibodies, as described in U.S. Pat. No. 6,150,584 and respective disclosures, which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP expression products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include, but are not limited to: F(ab')$_2$ fragments, which can be produced by pepsin digestion of an antibody molecule; and Fab fragments, which can be generated by reducing the disulfide bridges of F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well-known to those skilled in the art (see, e.g., Greenspan and Bona, 1993, FASEB J. 7:437–444; and Nisonoff, 1991, J. Immunol. 147:2429–2438). For example, antibodies that bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or fragments of such anti-idiotypes can be used in therapeutic regimens involving a NHP signaling pathway.

Additionally given the high degree of relatedness of mammalian NHPs, the presently described knock-out mice (having never seen a NHP, and thus never been tolerized to a NHP) have an unique utility, as they can be advantageously applied to the generation of antibodies against the disclosed mammalian NHPs (i.e., a NHP will be immunogenic in NHP knock-out animals).

5.4 Diagnosis of NHP-Mediated Disorders

A variety of methods can be employed for the diagnostic and prognostic evaluation of NHP-mediated disorders. These methods Such techniques include, for example, the use of restriction fragment length polymorphisms (RFLPs), which involve sequence variations in one or more of the recognition sites for any particular restriction enzyme used.

Additionally, improved methods for analyzing DNA polymorphisms that can be utilized for the identification of NHP gene mutations have been described that capitalize on the presence of variable numbers of short, tandemly repeated DNA sequences between certain restriction enzyme sites. For example, Weber (U.S. Pat. No. 5,075,217, which is incorporated herein by reference in its entirety) describes a DNA marker based on length polymorphisms in blocks of $(dC\text{-}dA)_n\text{-}(dG\text{-}dT)_n$ short tandem repeats. The average separation of $(dC\text{-}dA)_n\text{-}(dG\text{-}dT)_n$ blocks is estimated to be 30,000–60,000 bp. Markers that are so closely spaced exhibit a high frequency of co-inheritance, and are extremely useful in the identification of genetic mutations, such as, for example, mutations within a NHP gene, and the diagnosis of diseases and disorders related to NHP mutations.

Also, Caskey et al. (U.S. Pat. No. 5,364,759, which is incorporated herein by reference in its entirety) describe a DNA profiling assay for detecting short tri- and tetra-nucleotide repeat sequences. The process includes extracting the DNA of interest, amplifying the extracted DNA, and labeling the repeat sequences to form a genotypic map of the individual's DNA.

The level of NHP gene expression can also be assayed by detecting and measuring NHP transcription. For example, RNA from a cell type or tissue known to express, or suspected of expressing, a NHP gene may be isolated and tested utilizing hybridization or PCR techniques such as those described herein. The isolated cells can be derived from cell culture or from a patient sample. The analysis of cells taken from culture may be a necessary step in the assessment of cells to be used as part of a cell-based gene therapy technique or, alternatively, to test the effect of compounds on the expression of a NHP gene. Such analyses may reveal both quantitative and qualitative aspects of the expression pattern of a NHP gene, including activation or inactivation of NHP gene expression.

In one embodiment of such a detection scheme, cDNAs are synthesized from the RNAs of interest (e.g., by reverse transcription of the RNA molecule into cDNA). A sequence within the cDNA is then used as the template for a nucleic acid amplification reaction, such as a PCR amplification reaction, or the like. For detection of the amplified product, the nucleic acid amplification may be performed using radioactively or non-radioactively labeled nucleotides. Alternatively, enough amplified product may be made such that the product may be visualized by utilizing standard ethidium bromide staining or any other suitable nucleic acid staining method.

Additionally, it is possible to perform such NHP gene expression assays in situ, i.e., directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, 1992, "PCR In Situ Hybridization: Protocols And Applications", Raven Press, N.Y.). Alternatively, if a sufficient quantity of the appropriate cells can be obtained, standard Northern analysis can be performed to determine the level of mRNA expression of a NHP gene.

Additionally, NHP oligonucleotide or polynucleotide sequences can be used as hybridization probes in conjunction with a solid support matrix/substrate (e.g., resins, beads, membranes, plastics, polymers, metal or metallized substrates, gene chips, and crystalline or polycrystalline substrates, etc.).

5.4.2 Detection of NHP Gene Products

Antibodies directed against wild-type or mutant NHP gene products, or conserved variants or peptide fragments thereof, which are discussed above, may also be used in diagnostic and prognostic assays, as described herein. Such diagnostic methods may be used to detect abnormalities in the level of NHP gene expression, or abnormalities in the structure and/or temporal, tissue, cellular, or subcellular location of a NHP, and may be performed in vivo or in vitro, such as, for example, on biopsy tissue.

For example, antibodies directed to epitopes of a NHP can be used in vivo to detect the pattern and level of expression of a NHP in the body. Such antibodies can be labeled, e.g., with a radio-opaque or other appropriate compound, and injected into a subject, in order to visualize binding to a NHP expressed in the body, using methods such as X-rays, CAT-scans, or MRI. Labeled antibody fragments, e.g., a Fab or single chain antibody comprising the smallest portion of the antigen binding region, may be preferred for this purpose, to promote crossing the blood-brain barrier and permit labeling of a NHP expressed in the brain. Additionally, any NHP fusion protein or NHP conjugated protein whose presence can be detected can be administered. For example, NHP fusion or conjugated proteins labeled with a radio-opaque or other appropriate compound can be administered and visualized in vivo, as discussed above for labeled antibodies. Further, NHP fusion proteins, such as alkaline phosphatase-NHP or NHP-alkaline phosphatase fusion proteins, can be utilized for in vitro diagnostic procedures.

Alternatively, immunoassays or fusion protein detection assays can be utilized on biopsy and autopsy samples in vitro to permit assessment of the expression pattern of a NHP. Such assays can include the use of antibodies directed to epitopes of any of the domains of a NHP. The use of each or all of these labeled antibodies will yield useful information regarding translation and intracellular transport of a NHP, and can identify alterations in processing.

The tissue or cell type to be analyzed will generally include those that are known to express, or suspected of expressing, a NHP gene. The protein isolation methods employed herein may, for example, be such as those previously described (Harlow and Lane, 1988, supra). The isolated cells can be derived from cell culture or from a patient. The analysis of cells taken from culture may be a necessary step in the assessment of cells that could be used as part of a cell-based gene therapy technique or, alternatively, to test the effect of compounds on the expression of a NHP gene.

For example, antibodies, or fragments of antibodies, useful in the present invention may be used to quantitatively or qualitatively detect the presence of NHP gene products, or conserved variants or peptide fragments thereof. This can be accomplished, for example, by immunofluorescence techniques employing a fluorescently labeled antibody coupled with light microscopic, flow cytometric, or fluorimetric detection.

The antibodies (or fragments thereof) or NHP fusion or conjugated proteins useful in the present invention may, additionally, be employed histologically, as in immunofluorescence, immunoelectron microscopy or non-immuno assays, for in situ detection of NHP gene products or conserved variants or peptide fragments thereof. In situ detection may be accomplished by removing a histological specimen from a patient, and applying thereto a labeled antibody or fusion protein of the present invention. The antibody (or fragment) or fusion protein is preferably applied by overlaying the labeled antibody (or fragment) onto a biological sample. Through the use of such a procedure, it is possible to determine not only the presence of a NHP gene product, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for NHP gene products, or conserved variants or peptide fragments thereof, will typically comprise incubating a sample, such as a biological fluid, a tissue extract, freshly harvested cells, or lysates of cells that have been incubated in cell culture, in the presence of a detectably labeled antibody capable of identifying NHP gene products, or conserved variants or peptide fragments thereof, and detecting the bound antibody by any of a number of techniques well-known in the art. The biological sample may be brought in contact with and immobilized onto a solid phase support or carrier such as nitrocellulose, or other solid support that is capable of immobilizing cells, cell particles or soluble proteins. The support may then be washed with suitable buffers, followed by treatment with the detectably labeled NHP antibody or NHP fusion protein. The solid phase support may then be washed with the buffer a second time to remove unbound antibody or fusion protein. The amount of bound label on solid support may then be detected by conventional means.

The terms "solid phase support or carrier" are intended to include any support capable of binding an antigen or an antibody. Well-known supports or carriers include, but are not limited to, glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat, such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of NHP antibody or NHP fusion protein may be determined according to well-known methods. Those skilled in the art will be able to determine operative and optimal assay conditions for each determination by employing routine experimentation.

With respect to antibodies, one of the ways in which a NHP antibody can be detectably labeled is by linking the same to an enzyme for use in an enzyme immunoassay (EIA; see, for example, Gosling, ed., 2000, "Immunoassays: A Practical Approach", Oxford University Press, Inc., N.Y.). The enzyme that is bound to the antibody will react with an appropriate substrate, preferably a chromogenic substrate, in such a manner as to produce a chemical moiety that can be detected, for example, by spectrophotometric, fluorimetric or visual means. Enzymes that can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Additionally, detection may also be accomplished using any of a variety of other immunoassays. For example, by radioactively labeling the antibodies or antibody fragments, it is possible to detect NHPs through the use of a radioimmunoassay (RIA). The radioactive isotope can be detected by such means as the use of a gamma or scintillation counter, or by autoradiography.

It is also possible to label the antibody with a fluorescent compound. When the fluorescently labeled antibody is exposed to light of the proper wavelength, its presence can then be detected due to fluorescence. Exemplary fluorescent labeling compounds include, but are not limited to, fluorescein isothiocyanate, rhodamine, phycoerythrin, phycocyanin, allophycocyanin, o-phthaldehyde and fluorescamine. The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds include, but are not limited to, luminol, isoluminol, theromatic acridinium ester, imidazole, acridinium salt and oxalate ester.

Likewise, a bioluminescent compound may be used to label the NHP antibodies of the present invention. Bioluminescence is a type of chemiluminescence found in biological systems, in which a catalytic protein increases the efficiency of the chemiluminescent reaction. The presence of a bioluminescent protein is determined by detecting the presence of luminescence. Exemplary bioluminescent compounds for purposes of labeling include, but are not limited to, luciferin, luciferase and aequorin (green fluorescent protein; as described in U. S. Pat. Nos. 5,491,084, 5,625,048, 5,777,079, 5,795,737, 5,804,387, 5,874,304, 5,968,750, 5,976,796, 6,020,192, 6,027,881, 6,054,321, 6,096,865, 6,146,826, 6,172,188 and 6,265,548, each of which is hereby incorporated by reference).

5.5 Screening Assays for Compounds that Modulate NHP Expression or Activity

The following assays are designed to identify compounds that interact with (e.g., bind to) NHPs, compounds that interact with (e.g., bind to) intracellular proteins that interact with NHPs, compounds that interact with (e.g., bind to) both intracellular and extracellular proteins or receptors that regulate NHP activity and expression, compounds that interfere with the interaction of NHPs or proteins or compounds involved in NHP-mediated activity, and compounds that modulate the activity of a NHP gene (i.e., modulate the level of NHP gene expression) or modulate the level of NHPs. Assays may additionally be utilized that identify compounds that bind to NHP gene regulatory sequences (e.g., promoter sequences) and that may modulate NHP gene expression.

The compounds that can be screened in accordance with the present invention include, but are not limited to, peptides, antibodies and fragments thereof, and other organic compounds (e.g., peptidomimetics, small organic compounds) that bind to a NHP and either mimic or increase the activity of a NHP (i.e., agonists) or inhibit the activity of a NHP (i.e., antagonists); as well as peptides, antibodies or fragments thereof, and other organic compounds that mimic or increase NHP activity or inhibit the activity of a NHP.

Such compounds may include, but are not limited to, peptides such as, for example, soluble peptides, including, but not limited to, members of random peptide libraries (see, e.g., Lam et al., 1991, Nature 354:82–84; Houghten et al., 1991, Nature 354:84–86), and combinatorial chemistry-derived molecular libraries made of D- and/or L-configuration amino acids, phosphopeptides (including, but not limited to, members of random or partially degenerate, directed phosphopeptide libraries; see, e.g., Songyang et al., 1993, Cell 72:767–778), antibodies (including, but not limited to, polyclonal, monoclonal, humanized, anti-idiotypic, chimeric or single chain antibodies, and Fab, F(ab')$_2$ and Fab expression library fragments, and epitope-binding fragments thereof), and small organic or inorganic molecules.

Other compounds that can be screened in accordance with the invention include, but are not limited to, small organic molecules that are able to gain entry into an appropriate cell and affect the expression of a NHP gene, or some other gene involved in a NHP pathway (e.g., by interacting with the regulatory region or transcription factors involved in gene expression); or such compounds that affect the activity of NHPs or the activity of some other intracellular factor involved in a NHP pathway.

Computer modeling and searching technologies permit identification of compounds, or the improvement of already identified compounds, that can modulate NHP expression or activity. Having identified such a compound or composition, the active sites or regions are identified. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found. Next, the three dimensional geometric structure of the active site is determined. This can be done by known methods, including X-ray crystallography, which can determine a complete molecular structure. On the other hand, solid or liquid phase NMR can be used to determine certain intramolecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method can be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or a combination thereof, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. The compounds found from such a search are potential NHP modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites of NHPs, and related transduction and transcription factors, will be apparent to those of skill in the art.

Examples of molecular modeling systems are the CHARMM and QUANTA programs (Polygen Corporation, Waltham, Mass.). CHARMM performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen et al., 1988, Acta Pharmaceutical Fennica 97:159–166; Ripka, New Scientist 54–57 (Jun. 16, 1988); McKinaly and Rossmann, 1989, Ann. Rev. Pharmacol. Toxiciol. 29:111–122; Perry and Davies, OSAR: Quantitative Structure-Activity Relationships in Drug Design, pp. 189–193 (Alan R. Liss, Inc. 1989); Lewis and Dean, 1989, Proc. R. Soc. Lond. 236:125–140 and 141–162; and, with respect to a model receptor for nucleic acid components, Askew et al., 1989, J. Am. Chem. Soc. 111:1082–1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to the design of drugs specific to regions of DNA or RNA, once that region is identified.

Although described above with reference to design and generation of compounds that could alter binding, one could also screen libraries of known compounds, including natural products or synthetic chemicals, and biologically active materials, including proteins, for compounds that are inhibitors or activators of NHPs.

Compounds identified via assays such as those described herein may be useful, for example, in further elaborating the biological function of a NHP gene product, and for ameliorating NHP-related disorders.

5.5.1 In Vitro Screening Assays for Compounds that Bind to a NHP

In vitro systems may be designed to identify compounds capable of interacting with (e.g., binding to) NHPs. The compounds thus identified (such as NHP modulators, natural NHP substrates, etc.) can be useful, for example, in modulating the activity of wild-type and/or mutant NHP gene products; in elaborating the biological function of NHPs; in screens for identifying compounds that disrupt normal NHP interactions; or in themselves directly disrupt such interactions.

The principle of the assays used to identify compounds that bind to a NHP involves preparing a reaction mixture of a NHP and the test compound under conditions and for a time sufficient to allow the two components to interact and bind, thus forming a complex that can be removed and/or detected in the reaction mixture. The NHP species used can vary depending upon the goal of the screening assay. For example, where agonists of the natural ligand/substrate are sought, full length NHPs, or a soluble truncated NHP polypeptide that affords advantages in the assay system (e.g., labeling, isolation of the resulting complex, etc.) can be utilized.

The screening assays can be conducted in a variety of ways. For example, one method to conduct such an assay would involve anchoring a NHP protein, polypeptide, peptide, or fusion protein, or the test substance, onto a solid phase and detecting NHP/test compound complexes anchored on the solid phase at the end of the reaction. In one embodiment of such a method, the NHP reactant may be anchored onto a solid surface, and the test compound, which is not anchored, may be labeled, either directly or indirectly. Examples of some of the technologies available to immobilize the molecules are discussed in Cass, ed., "Immobilized Biomolecules In Analysis: A Practical Approach", Oxford University Press, N.Y.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored. molecular structure. Such a search seeks compounds having structures that match the determined active site structure and that interact with the groups defining the active site. Such a search can be manual, but is preferably computer assisted. The compounds found from such a search are potential NHP modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites of NHPs, and related transduction and transcription factors, will be apparent to those of skill in the art.

Examples of molecular modeling systems are the CHARMM and QUANTA programs (Polygen Corporation, Waltham, Mass.). CHARMM performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen et al., 1988, Acta Pharmaceutical Fennica 97:159–166; Ripka, New Scientist 54–57 (Jun. 16, 1988); McKinlay and Rossmann, 1989, Ann. Rev. Pharmacol. Toxiciol. 29:111–122; Perry and Davies, OSAR: employed for identifying proteins that interact with NHPs. Among the traditional methods that may be employed are co-immunoprecipitation, crosslinking and co-purification through gradients or chromatographic columns of cell lysates, or proteins obtained from cell lysates, and a NHP to identify proteins in the lysate that interact with NHPs. For these assays, the NHP component used can be a full length NHP, a peptide or polypeptide corresponding to one or more domains of a NHP, or a fusion protein containing one or more domains of a NHP. Once isolated, such an intracellular protein can be identified and can, in turn, be used in conjunction with standard techniques to identify proteins with which it interacts. For example, at least a portion of the amino acid sequence of an intracellular protein that interacts with a NHP can be ascertained using techniques well-known to those of skill in the art, such as via the Edman degradation technique (see, e.g., Creighton, 1983, supra, pp.34–49). The amino acid sequence obtained may be used as a guide for the generation of oligonucleotide mixtures that can be used to screen for gene sequences encoding such intracellular proteins. Screening may be accomplished, for example, by standard hybridization or PCR techniques. Techniques for the generation of oligonucleotide mixtures and screening are well-known (see, e.g., Ausubel, supra., and Innis et al., eds. "PCR Protocols: A Guide to Methods and Applications", 1990, Academic Press, Inc., N.Y.).

Additionally, methods may be employed that result in the simultaneous identification of genes that encode proteins that are capable of interacting with NHPs. These methods include, for example, probing expression libraries, in a manner similar to the well-known technique of antibody probing of lambda gt11 libraries, using a labeled NHP protein, polypeptide, peptide or fusion protein, e.g., a NHP polypeptide or NHP domain fused to a marker (e.g., an enzyme, fluor, luminescent protein, or dye), or an Ig-Fc domain.

One method that detects protein interactions in vivo, the two-hybrid system, is described in detail for illustration only and not by way of limitation. One version of this system utilizes yeast cells (Chien et al., 1991, Proc. Natl. Acad. Sci. USA, 88:9578–9582), while another uses mammalian cells (Luo et al., 1997, Biotechniques 22:350–352). Both the yeast and mammalian two-hybrid systems are commercially available from Clontech (Palo Alto, Calif.), and are further described in U.S. Pat. Nos. 5,283,173, 5,468,614, and 5,667,973, which are herein incorporated by reference in their entirety.

Briefly, utilizing such a system, plasmids are constructed that encode two hybrid proteins: one plasmid consists of nucleotides encoding the DNA-binding domain of a transcription activator protein fused to a NHP nucleotide sequence encoding a NHP protein, polypeptide, peptide or fusion protein, and the other plasmid consists of nucleotides encoding an activation domain of a transcription activator protein fused to a cDNA encoding an unknown protein to be tested for interaction with a NHP, which has been recombined into this plasmid as part of a cDNA library. The DNA-binding domain fusion plasmid and the cDNA library are transformed into a strain of the yeast Saccharomyces cerevisiae or a mammalian cell (such as Saos-2, CHO, CV1, Jurkat or HeLa) that contains a reporter gene (e.g., HBS, lacZ, CAT, or a gene encoding an essential amino acid synthetase) whose regulatory region contains the binding site of the transcription activator. Either hybrid protein alone cannot activate transcription of the reporter gene: the DNA-binding domain hybrid cannot because it does not provide activation function; and the activation domain hybrid cannot because it cannot localize to the binding site of the activator. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, a NHP may be used as the bait gene product. Total genomic or cDNA sequences are fused to DNA encoding an activation domain. This library and a plasmid encoding a hybrid of a bait NHP gene product fused to the DNA-binding domain are co-transformed into a reporter strain, and the resulting transformants are screened for those that express the reporter gene. For example, and not by way of limitation, a bait NHP sequence, such as an open reading frame of a NHP (or a domain of a NHP) can be cloned into a vector such that it is translationally fused to DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with a bait NHP gene product are to be detected can be made using methods routinely practiced in the art. According to one particular system, for example, the cDNA fragments can be inserted into a vector such that they are translationally fused to the transcriptional activation domain of GAL4. This library can be co-transformed along with the bait NHP gene-GAL4 fusion plasmid into a yeast strain that cannot grow without added histidine, and that contains a HIS3 gene driven by a promoter that contains GAL4 activation sequence. A cDNA encoded protein, fused to GAL4 transcriptional activation domain, which interacts with the bait NHP gene product will reconstitute an active GAL4 protein and thereby drive expression of the HIS3 gene. Colonies that express HIS3 can be detected by their growth on petri dishes containing semi-solid agar based media lacking histidine. The cDNA can then be purified from these strains, and used to produce and isolate the bait NHP gene-interacting protein using techniques routinely practiced in the art.

5.5.3 Assays for Compounds that Interfere with NHP Activity

The macromolecules that interact with NHPs are referred to, for purposes of this discussion, as "binding partners". These binding partners are likely to be involved in a NHP pathway, and therefore, may have a role in NHP-mediated disorders. Therefore, it is desirable to identify compounds that interfere with or disrupt the interaction of such binding partners with NHPs, and that may be useful in regulating the activity of NHPs and controlling NHP-mediated disorders.

The basic principle of the assay systems used to identify compounds that interfere with the interaction between a NHP and its binding partner or partners involves preparing a reaction mixture containing a NHP protein, polypeptide, peptide or fusion protein, and the binding partner under conditions and for a time sufficient to allow the components to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the NHP moiety and its binding partner(s). Control reaction mixtures are incubated without the test compound or with a placebo. The formation of complexes between the NHP moiety and the binding partner is then detected. The formation of a complex in the control reaction, but not in the reaction mixture containing the test compound, indicates that the compound interferes with the interaction of the NHP and the interactive binding partner. Additionally, complex formation within reaction mixtures containing the test compound and a normal NHP protein may also be compared to complex formation within reaction mixtures containing the test compound and a mutant NHP. This comparison may be important in those cases wherein it is desirable to identify compounds that disrupt interactions of mutant but not normal NHPs.

Assays for compounds that interfere with the interaction of NHPs and binding partner(s) can be conducted in a heterogeneous or homogeneous format. Heterogeneous assays involve anchoring either the NHP moiety product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction by competition can be identified by conducting the reaction in the presence of the test substance, i.e., by adding the test substance to the reaction mixture prior to or simultaneously with the NHP moiety and interactive binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the NHP moiety or the interactive binding partner is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of a NHP gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing), and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface, e.g., using a labeled antibody specific for the initially non-immobilized species (the antibody, in turn, may be directly labeled or indirectly labeled with a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected, e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. In this approach, a preformed complex of a NHP moiety and the interactive binding partner is prepared in which either the NHP or its binding partner is labeled, but the signal generated by the label is quenched due to formation of the complex (see, e.g., U.S. Pat. No. 4,109,496, incorporated herein by reference, which utilizes this approach for immunoassays). The addition of a test substance that competes with and displaces one of the species from the preformed complex will result in the generation of a signal above background. In this way, test substances that disrupt NHP/intracellular binding partner interactions can be identified.

In a particular embodiment, a NHP fusion protein can be prepared for immobilization. For example, a NHP, or a peptide fragment thereof, e.g., corresponding to one or more particular domain(s), can be fused to glutathione-S-transferase (GST) using a fusion vector, such as pGEX-5X-1, in such a manner that the GST binding activity is maintained in the resulting fusion protein. An interactive binding partner, identified as described herein, can be purified and used to raise polyclonal and monoclonal antibodies, using methods routinely practiced in the art. Such antibodies can be labeled with a radioactive isotope, $^{125}$I for example, by methods routinely practiced in the art. In a heterogeneous assay, such GST-NHP fusion proteins can be anchored to glutathione-agarose beads. The interactive binding partner can then be added in the presence or absence of the test compound in a manner that allows interaction and binding to occur. At the end of the reaction period, unbound material can be washed away, and a labeled monoclonal antibody that binds the binding partner can be added to the system and allowed to bind to complexed binding partner. The interaction between the NHP and the interactive binding partner can be detected by measuring the amount of radioactivity that remains associated with the glutathione-agarose beads. A successful inhibition of the interaction by the test compound will result in a decrease in measured radioactivity.

Alternatively, a GST-NHP fusion protein and an interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the NHP/binding partner interaction can be detected by adding a labeled antibody against the binding partner and measuring the radioactivity associated with the beads.

In another embodiment of the invention, where the binding partner is a protein, these same techniques can be employed using peptide fragments that correspond to one or more of the binding domains of a NHP and/or the interactive binding partner, in place of one or both of the full length proteins. Any number of methods routinely practiced in the art can be used to identify and isolate the binding domains or regions. These methods include, but are not limited to, mutagenesis of the gene encoding one of the proteins, and screening for disruption of binding in a co-immunoprecipitation assay. Compensating mutations in the sequence encoding the second species in the complex can then be selected. Sequence analysis of the sequences encoding the respective proteins will reveal the mutation(s) that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once a sequence encoding the binding partner is obtained, short polynucleotide segments can be engineered to express peptide fragments of the protein, which can then be tested for binding activity, and purified or synthesized.

For example, and not by way of limitation, a NHP protein, polypeptide or peptide can be anchored to a solid material, as described above, by making a GST-NHP fusion protein and allowing it to bind to glutathione agarose beads. The interactive binding partner can be labeled with a radioactive isotope, such as $^{35}S$, and cleaved with a proteolytic enzyme, such as trypsin. Cleavage products can then be added to the anchored GST-NHP fusion protein and allowed to bind. After washing away unbound peptides, labeled bound material, representing the intracellular binding partner binding domain, can be eluted, purified, and analyzed to determine the amino acid sequence by well-known methods. Peptides so identified can be produced synthetically or fused to appropriate facilitative proteins using recombinant DNA technology.

5.5.4 The Use of Compounds to Treat NHP-Mediated Disorders

The invention also encompasses the use of agonists and antagonists of a NHP (including small molecules and large molecules), mutant versions of a NHP or portions thereof that compete with native NHPs, peptides, and antibodies, as well as nucleotide sequences that can be used to inhibit the expression of a NHP (e.g., antisense and ribozyme molecules, and gene or regulatory sequence replacement constructs) or to enhance the expression of NHP polynucleotides (e.g., expression constructs that place the described polynucleotide under the control of a strong promoter system) in the treatment of NHP-mediated disorders. Compounds including, but not limited to, those identified via assay techniques such as those described above, can be tested for the ability to ameliorate symptoms associated with NHP-mediated disorders.

The assays described above can identify compounds that affect NHP activity, or compounds that affect NHP gene activity (by affecting NHP gene expression, including molecules, e.g., proteins or small organic molecules, that affect or interfere with splicing events so that expression of a full length or a truncated form of a NHP can be modulated). However, it should be noted that the assays described can also be used to identify compounds that indirectly modulate NHPs. The identification and use of compounds that affect a NHP-independent step in a NHP pathway are also within the scope of the invention. Compounds that indirectly affect NHP activity can also be used as part of a therapeutic method for the treatment of NHP-mediated disorders.

The invention additionally encompasses cell-based and animal model-based assays for the identification of compounds exhibiting an ability to ameliorate the symptoms of NHP-mediated disorders. Cell-based systems used to identify compounds that may act to ameliorate NHP-mediated disorder symptoms can include, for example, recombinant or non-recombinant cells, such as cell lines that express a NHP sequence. Host cells (e.g., COS cells, CHO cells, fibroblasts) genetically engineered to express a functional NHP can also be used. The presence of a functional NHP can be determined, for example, by a chemical or a phenotypic change, the induction of another host cell gene, a change in ion flux (e.g., $Ca^{++}$), or tyrosine phosphorylation of host cell proteins, etc.

In utilizing such cell systems, cells may be exposed to a compound suspected of exhibiting an ability to ameliorate the symptoms of NHP-mediated disorders, at a sufficient concentration and for a time sufficient to elicit such an amelioration of the symptoms of NHP-mediated disorders in the exposed cells. After exposure, the cells can be assayed to measure alterations in NHP expression, e.g., by assaying cell lysates for NHP mRNA transcripts (e.g., by Northern analysis or RT-PCR), or by assaying for the level of a NHP protein expressed in the cell (e.g., by SDS-PAGE and Western blot or immunoprecipitation); compounds that regulate or modulate NHP expression are good candidates as therapeutics. Alternatively, the cells can be examined to determine whether one or more NHP disorder-like cellular phenotype has been altered to resemble a more normal or more wild-type, non-NHP disorder phenotype, or a phenotype more likely to produce a lower incidence or severity of disorder symptoms. Still further, the expression and/or activity of components of the signal transduction pathway(s) of which a NHP is a part, or the activity of a NHP signal transduction pathway itself, can be assayed.

In addition, animal-based NHP-mediated disorder systems may be used to identify compounds capable of treating or ameliorating symptoms associated with NHP-mediated disorders. These animals may be transgenic, knockout, or knock-in (preferably humanized knock-ins where, for example, the endogenous animal NHP gene has been replaced by a human NHP sequence) animals, as described herein. Such animal models may be used as test substrates for the identification of drugs, pharmaceuticals, therapies and interventions that may be effective in treating such disorders. For example, animal models can be exposed to a compound suspected of exhibiting an ability to ameliorate symptoms of NHP-mediated disorders, at a sufficient concentration and for a time sufficient to elicit such an amelioration of NHP disorder associated symptoms in the exposed animals. The response of the animals to the exposure may be monitored by assessing the reversal of symptoms associated with NHP-mediated disorders. With regard to intervention, any treatments that reverse, halt or slow the progression of any aspect of symptoms associated with NHP disorders should be considered as candidates for therapeutic intervention in treatment of human NHP disorders. Dosages of test agents may be determined by deriving toxicity and dose-response curves.

5.6 Pharmaceutical Preparations and Methods of Administration

Compounds that are determined to affect expression of the sequences of the current invention, or the interaction of the peptides and proteins of the present invention with any of their binding partners, can be administered to a patient at therapeutically effective doses to treat or ameliorate low white blood cell counts. A therapeutically effective dose refers to that amount of the compound sufficient to result in any delay in onset, amelioration or retardation of disease symptoms.

5.6.1 Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. Compounds that exhibit toxic side effects may be used in certain embodiments, however care should usually be taken to design delivery systems that target such compounds preferentially to the site of affected tissue, in order to minimize potential damage to uninfected cells and, thereby, reduce side effects.

The data obtained from cell culture assays and animal studies can be used in formulating a range of dosages for use in humans. The dosages of such compounds lie preferably within a range of circulating concentrations that include the $ED_{50}$ with little or no toxicity. The dosage may vary within this range depending upon the dosage form employed and the route of administration utilized. For any compound used in the methods of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

When the therapeutic treatment of disease is contemplated, the appropriate dosage may also be determined using animal studies to determine the maximal tolerable dose, or MTD, of a bioactive agent per kilogram weight of the test subject. In general, at least one animal species tested is mammalian. Those skilled in the art regularly extrapolate doses for efficacy and avoiding toxicity to other species, including human. Before human studies of efficacy are undertaken, Phase I clinical studies in normal subjects help establish safe doses.

Additionally, the bioactive agent may be complexed with a variety of well established compounds or structures that, for instance, enhance the stability of the bioactive agent, or otherwise enhance its pharmacological properties (e.g., increase in vivo half-life, reduce toxicity, etc.).

The therapeutic agents will be administered by any number of methods known to those of ordinary skill in the art including, but not limited to, inhalation; subcutaneous (sub-q); intravenous (I.V.); intraperitoneal (I.P.); intramuscular (I.M.), or intrathecal injection; or topically applied (transderm, ointments, creams, salves, eye drops, and the like).

5.6.2 Formulations and Use

Pharmaceutical compositions for use in accordance with the present invention may be formulated in conventional manners using one or more physiologically acceptable carriers or excipients.

Thus, the compounds and their physiologically acceptable salts and solvates may be formulated for administration by inhalation or insufflation (either through the mouth or the nose), or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring agents, coloring agents and sweetening agents as appropriate.

Preparations for oral administration may be suitably formulated to give controlled release of the active compound. For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated as compositions for rectal administration such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil), ion exchange resins, or as sparingly soluble derivatives, for example, as a sparingly soluble salt. The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration.

The examples below are provided to illustrate the subject invention. These examples are provided by way of illustration only, and are not included for the purpose of limiting the invention in any way whatsoever.

6.0 EXAMPLES 6.1 NHP Gene Disrupted Mice

Gene trapping is a method of nonspecific insertional mutagenesis that uses a fragment of DNA coding for a reporter or selectable marker gene as a mutagen. Gene trap vectors have been designed to integrate into introns or exons in a manner that allows the cellular splicing machinery to splice vector encoded exons to cellular mRNAs. Commonly, gene trap vectors contain selectable marker sequences that are preceded by strong splice acceptor sequences and are not preceded by a promoter. Thus, when such vectors integrate into a gene, the cellular splicing machinery splices exons from the trapped gene onto the 5' end of the selectable marker sequence. Typically, such selectable marker genes can only be expressed if the vector encoding the gene has integrated into an intron. The resulting gene trap events are subsequently identified by selecting for cells that can survive selective culture.

Embryonic stem cells (Lex-1 cells derived from murine strain 129SvEv$^{Brd}$) were mutated by a process involving the insertion of at least a portion of a genetically engineered vector sequence into the NHP gene. The mutated embryonic stem cells were then microinjected into blastocysts, which were subsequently introduced into pseudopregnant female hosts and carried to term using established methods, such as those described in, for example, Zambrowicz et al., eds., "Mouse Mutagenesis", 1998, Lexicon Press, The Woodlands, Tex., and periodic updates thereof, herein incorporated by reference. In this case, the virus inserted in the forward orientation, close to the nucleotides coding for amino acid 135, and disrupted the NHP gene. The resulting chimeric animals were subsequently bred to produce offspring capable of germline transmission of an allele containing the engineered mutation in the NHP gene.

Techniques useful to disrupt a gene in a cell, and especially an ES cell, that may already have a disrupted gene are disclosed in U.S. Pat. Nos. 6,136,566, 6,139,833 and 6,207,371, and U.S. patent application Ser. No. 08/728,963, each of which are hereby incorporated herein by reference in their entirety.

6.1.1 The Effect of NHP Disruption on Mouse Physiology

The genetic distribution of wild-type (11), heterozygous (28) and homozygous (19) animals appears to be normal. Thus, for the remaining studies, mice homozygous for the disruption of the NHP gene were studied in conjunction with heterozygous and wild-type litter mates. During this analysis, the mice were subjected to a medical work-up using an integrated suite of medical diagnostic procedures designed to assess the function of the major mammalian organ systems in the subject. By studying numerous mice in which the NHP gene had been disrupted, in conjunction with wild-type litter mates, more reliable and repeatable data was obtained. Disruption of the NHP gene resulted in, among other effects, an unexpected increase in white blood cell counts, as described in greater detail below. The disruption of the NHP gene was confirmed by RT-PCR.

Additional studies of the expression patterns of human and murine NHPs showed that the NHPs can be detected in certain mouse and human tissues by RT-PCR. NHP transcripts were detected in mouse tissue derived from mouse brain, thymus, and heart. NHP transcripts were detected in human tissue derived from human prostate and testis.

6.1.2 Size, Percent Body Fat, and Bone Mineral Density of NHP Knockouts

Body composition and percent body fat was measured by dual energy X-ray absorptiometry (DEXA) using the Piximus small animal densitometer (Lunar Corporation, Madison, Wis.). Individual mice were sedated with Avertin (1.25% solution, 2.5 mg/10 gm body weight delivered by intraperitoneal injection), immobilized on a positioning tray and then placed on the Piximus imaging window. All scans were performed using the total body mode (0.18×0.18 mm), and the analysis was performed on the total body region of interest. The entire body, except the head, of each mouse was exposed for 5 minutes to a cone shaped beam of both high and low energy x-rays. A high-resolution digital picture was taken of the image of the x-rays hitting a luminescent panel. Lunar PIXImus software (version 1.45) was used to calculate the ratio of attenuation of the high and low energies to separate bone from soft tissue compartments and, within the soft tissue compartment, to separate lean tissue mass from fat mass and thus determine the bone mineral density (BMD), volumetric bone mineral density (vBMD), total bone mineral content (BMC), fat composition (% fat), lean body mass (LBM), the ratio of BMC/LBM, and total tissue mass (TTM) in the regions of interest (total body for all tests, and additionally, vertebrae and both femurs for BMD). Previous studies have determined that this technique precisely measures fat and lean tissue mass, and that there is a close relationship between fat and lean tissue mass estimated by this technique with those measured using chemical carcass analysis (Nagy and Clair, 2000, Obesity Research 8:392–398).

Body composition and percent body fat was measured in eight (8) homozygous (6 males, 2 females), four (4) heterozygous (2 males and 2 females), and four (4) wild-type (2 males and 2 females) mice. The mean percent total body fat was notably decreased in both the male and female (−/−) mice compared to the (+/−) and (+/+) animals. However, the values for the (−/−) animals fell within historical normal ranges. There was no difference between groups in any of the other parameters measured (TTM, LBM, vBMD, total body BMD, femur BMD, vertebrae BMD, total body BMC, and the BMC/LBM ratio).

Mouse body weight was determined to the nearest 0.1 gm using an Ohaus Scout scale. Body length was determined from nose to the base of tail and is reported in cm. Body weight and body length data were obtained for mice at eight (8) weeks of age. The body weight of eight (8) homozygous (6 males, 2 females), four (4) heterozygous (2 males and 2 females), and four (4) wild-type (2 males and 2 females) mice was determined and analyzed. Decreased body weight was noted for the two female (−/−) mice compared to the female (+/+) and (+/−) mice.

Body length data was determined and analyzed for eight (8) homozygous (6 males, 2 females), four (4) heterozygous (2 males and 2 females), and four (4) wild-type (2 males and 2 females) mice. There was no significant difference in body length between groups.

6.1.3 The Effect of NHP Disruption on Hematology and Blood Chemistry

Whole blood was collected by retro-orbital bleed and placed in a capillary blood collection tube that contained EDTA. The blood was analyzed using the Cell-Dyn 3500R analyzer (Abbott Diagnostics). The analyzer employs dual technologies to provide the basis for a five-part white blood cell (WBC) differential identification. Multi-Angle Polarized Scatter Separation (MAPSS) provides the primary white blood cell count and differential information, while impedance provides additional information in the presence of fragile lymphocytes and hypotonically resistant red blood cells. Approximately 135 microliters of whole blood is aspirated into the analyzer using a peristaltic pump. Four independent measurement techniques are used by the Cell-Dyn 3500R System to obtain the hematologic parameters. The WBC Optical Count (WOC) and the WBC differential data are measured in the optical flow channel, resulting in the identification of the WBC subpopulations (neutrophils, lymphocytes, monocytes, eosinophils, and basophils) for the five part WBC differential. The WBC Impedance Count (WIC) is measured in one electrical impedance channel. The RBC and platelet data are measured in a second electrical impedance channel. The hemoglobin is measured in the spectrophotometric channel. The sample was aspirated, diluted, mixed, and the measurements for each parameter were obtained during each instrument cycle. The final hematological analysis parameters obtained are white blood cell count, neutrophils, lymphocytes, monocytes, eosinophils, basophils, red blood cells, hemoglobin, hematocrit, platlets, red cell distribution width, mean corpuscular volume, mean corpuscular hemoglobin, mean corpuscular hemoglobin concentration and mean platelet volume.

Blood samples were obtained from a total of sixteen (16) mice; eight (8) homozygous (6 males, 2 females), four (4) heterozygous (2 males and 2 females), and four (4) wild-type (2 males and 2 females) mice. Analysis and comparison of the blood samples revealed that disruption of the NHP gene results in an upward trend in mean white blood cell (WBC) counts, with subsequent increases in absolute neutrophil (NEUTRO), lymphocyte (LYM), monocyte (MONO), eosinophil (EOS) and basophil (BASO) counts in the (−/−) and (+/−) mice. The WBC values for the +/+ mice were 5.9±2.3, for the +/− mice were 9.7±0.7, and for the −/− mice were 9.6±2.8. The NEUTRO values for the +/+ mice were 0.91±0.29, for the +/− mice were 1.40±0.39, and for the −/− mice were 1.26±0.34. The LYM values for the +/+ mice were 4.61±2.03, for the +/− mice were 7.70±0.53, and for the −/− mice were 7.83±2.58. The MONO values for the +/+ mice were 0.30±0.13, for the +/− mice were 0.53±0.19, and for the −/− mice were 0.42±0.18. The EOS values for the +/+ mice were 0.033±0.030, for the +/− mice were 0.063±0.050, and for the −/− mice were 0.050±0.059. The BASO values for the +/+ mice were 0.008±0.008, for the +/− mice were 0.016±0.009, and for the −/− mice were 0.018±0.010. However, the relative distribution of these cells remained normal.

Approximately 200 microliters of whole blood was collected from the retro-orbital plexus. The blood was placed in a 2.5 ml micro-collection tube and centrifuged to obtain the serum. The sample was analyzed for the following analytes: albumin, alkaline phosphatase, alanine aminotransferase (ALT), total bilirubin, blood urea nitrogen (BUN), calcium, glucose, phosphorus, cholesterol, triglycerides, creatinine and uric acid using a Cobas Integra 400 (Roche Diagnostics). The Cobas Integra 400 is a random and continuous access, sample selective analyzer. The analyzer uses four measuring principles: absorbance photometry, turbidimetry, fluorescence polarimetry and ion-selective electrode potentiometry to assay the analytes described above.

A total of sixteen (16) mice were analyzed; eight (8) homozygous (6 males, 2 females), four (4) heterozygous (2 males and 2 females), and four (4) wild-type (2 males and 2 females) mice. There were no significant differences in any of the above analytes between the three groups.

The mononuclear cell profile is derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples are analyzed using a Becton Dickinson FACSCalibur flow cytometer with CellQuest software. All leukocytes are identified by CD45 staining, and granulocytes are excluded by scatter. T cells are identified by expression of TCR b-chain, and are further divided into CD4+CD8− (mature helper) and CD4−CD8+ (mature cytotoxic/suppressor). NK cells and B cells are identified from the TCRb− (non-T) population by staining with pan-NK and CD19 antibody, respectively. Monocytes are defined as CD45+mononuclear cells which are negative for all T, B, and NK markers.

A total of six (6) mice were analyzed: two (2) wild-type (+/+); two (2) heterozygotes (+/−); and two (2) homozygotes. There were no significant differences in the percentage of CD4+CD8− or CD4−CD8+ cells, the CD4+/CD8+ ratio, or the percentage of B cells or monocytes between the two groups.

Additionally, quantitative insulin assays were performed on of eight (8) homozygous mice (6 males and 2 females) and four (4) wild-type mice (2 males and 2 females) using a Cobra II Series Auto-Gamma Counting System to determine the insulin levels. There was no significant difference in the insulin levels between the two groups of mice.

6.1.4 Urinalysis

Approximately 100 microliters of urine was collected by placing the mouse in a clean cage lined with aluminum foil and carefully watching the mouse for urination. Immediately following urination, the sample was collected into a micro-collection tube. The specimen was analyzed using a calibrated Chemstrip 101 Urine Analyzer (Ames Diagnostics) urinalysis test strip. The urine was placed on the test pad and was read as indicated by the manufacturer according to the package insert. This urinalysis determines urine osmolality, the presence of leukocytes, nitrite, protein, glucose, ketones, urobilinogen, bilirubin and blood.

Urine samples were obtained from fifteen (15) mice; eight (8) homozygous (6 males, 2 females), four (4) heterozygous (2 males and 2 females), and three (4) wild-type (2 males and 1 female) mice. Analysis and comparison of the urine samples revealed abnormal protein levels (30 mg/dl) in 5 of the 8 homozygous mice (compared to only 1 of the 4 heterozygous and 1 of the 3 wild-type mice), and abnormal ketone levels in 6 of the 8 homozygous mice (compared to only 1 of the 4 heterozygous and 1 of the 3 wild-type mice). No differences between the groups in the other analytes were detected.

6.1.5 Opthalmology

Slit Lamp Analysis: The slit lamp is a biomicroscope that allows examination of the anatomy of the anterior eye segment, as well as the localization of some abnormalities. It is a rapid and convenient method for preliminary eye examination prior to fundus photography. Mouse eye analysis began with examination utilizing a slit lamp (Nikon, Tokyo, Japan) in combination with a 60 or 90 diopter (D) condensing lens. In preparation for examination, mouse pupils were dilated by adding a drop of 1% cyclopentolate and 1% atropine (Alcon Laboratory Inc., Fort Worth, Tex.) to each eye.

Fundus Photography: Fundus photography is a noninvasive method of examining the eye that is adaptable to high throughput analysis. The appearance of the ocular fundus is representative of overall health. Variation in the appearance of the ocular fundus can be indicative of different diseases, including, but not limited to, diabetes, obesity, cardiovascular disorders, angiogenesis, oxidant related disorders and cancer. Selected animals were subjected to fundus photography using a Kowa Genesis small animal fundus digital camera (Tokyo, Japan) to photograph mouse fundi. The instrument was used with a condensing lens, Volk 60D or 90D (Mentor, Ohio, USA), mounted between the camera and the object to be viewed (mouse eye). In order to avoid complications of anesthesia, such as clouding of the ocular media, photographs were obtained on conscious mice, whose vibrissae were trimmed with fine scissors to prevent them from obscuring the photograph.

Retinal Angiography: Fluorescein angiography is an established technique used to examine the circulation of the retina. In particular it enables the progression of diabetic retinopathy to be monitored, and provides valuable information on the presence or absence of vascular lesions such as edema (leakage) and ischemia (occlusion of the capillaries). The retinal angiography procedure was similar to the procedure used for fundus photography, except that the standard light was replaced with blue light in combination with a barrier filter. To facilitate imaging, mice were injected intraperitoneally with 25% sodium fluorescein (Akorn Inc., Decator, Ill.) at a dose of 0.01 ml per 5–6 gm body weight. For viewing, the eyepiece was fitted with the manufacturer-supplied barrier filter. The digital imaging system used consists of a camera, a computer, and Komit+ software (Kowa, Tokyo, Japan) especially designed for ophthalmological applications, which facilitates image data acquisition, analysis and storage.

The artery to vein ratio (A/V) is the ratio of the artery diameter to the vein diameter (measured before the bifurcation of the vessels). The A/V ratio is measured and calculated according to fundus images. Many diseases will influence the ratio, i.e., diabetes, cardiovascular disorders, papilledema and optic atrophy.

Ophthalmological analysis was performed on sixteen (16) mice; eight (8) homozygous (6 males, 2 females), four (4) heterozygous (2 males and 2 females), and four (4) wild-type (2 males and 2 females). The analysis revealed no significant ophthalmological differences between mice with or without functional NHP alleles, with the exception of an increased retinal arteriolar light reflex (ALR) noted in 4/8 (−/−) mice compared to the (+/+) mice, indicating abnormal thickening of the arteriolar wall. Additionally, 1/8 (−/−) mice had a subcapsular cataract.

6.1.6 Neurological and Behavioral Analysis

Functional Observational Battery (FOB): A subset of tests from the Irwin neurological screen (Irwin, 1968, Psychopharmacologia 13:222–257) were used to evaluate the gross neurological function of the mice. This battery of simple neurological tests took 10 minutes and was useful for detecting severe neurological impairments.

Mice were first examined for their overall physical characteristics, such as presence of whiskers, bald patches, piloerection, exopthalmus, palpebral closure, kyphosis, lordosis, and tail abnormalities. The mice were then placed into an empty cage for one minute. Any abnormal spontaneous behaviors such as wild-running, excessive grooming, freezing behavior, hunched body posture when walking, etc., were recorded. Mice were next placed into an empty cage to assess motor reflexes. The cage was quickly moved side to side and up and down. The normal postural reflex is to extend all four legs in order to maintain an upright, balanced position. The righting reflex was measured by turning the mice on their back and determining how long it took the mice to return to an upright position. Normal mice will immediately right themselves. If a mouse did not right itself within 60 seconds, the mouse was returned to its normal upright position.

The eye blink reflex, ear twitch reflex, and flank reflex were measured by lightly touching the eye, tip of the ear, and torso once each with a thin clear piece of plastic. The whisker-orienting response was measured by lightly touching the whiskers with a thin clear piece of plastic while the animal was allowed to move freely. The whiskers are typically moving. When touched the whiskers of normal mice will stop moving and in many cases the mouse will turn its head to the side where the whiskers were touched. To determine a mouse's visual response to light, the mouse was examined in a dimly lit room. Pupil constriction and dilation reflexes were measured by quickly directing a penlight at the mousers eye and observing pupil constriction and subsequently pupil dilatation once the light source was removed.

The visual reaching response was measured by suspending a mouse by its tail and moving it down towards the edge of a cage. A mouse that can see the cage will reach towards it when the cage is moved in the direction of the mouse.

The tail suspension response was determined by holding the mouse approximately six inches in the air by the tail for 20 seconds and recording normal behaviors such as grabbing of the hindlimbs with the forelimbs and turning up on its sides. If present, abnormal behaviors such as hindlimb and forelimb clutch were also recorded.

The cateleptic response was measured by using a small rod at a fixed vertical position. The mouse was positioned such that its forelimbs were resting on the rod. Normal mice in this situation will quickly remove their forelimbs from the rod. A 60 second time limit was allowed, after which a non-responsive mouse was returned to its normal posture.

The olfactory response was tested by using an odor such as vanilla extract as an olfactory cue. A small amount of vanilla was placed on cotton swab and held behind and to the side of a mouse. If the mouse turns and orients itself to the position of the vanilla extract-containing cotton swab, the result is interpreted as an indication that the mouse can smell this olfactory cue.

Mouse body temperature was determined by gently inserting a small probe into the rectum and recording the temperature with a digital read-out (Physitemp, Clifton). This process took less than 5 sec and the mice appeared calm and unstressed throughout the procedure.

This entire battery of simple neurological tests took about 10 minutes and provided for the detection of severe neurological impairment. At the completion of these tests the mice were returned to their home cage.

Hot Plate Assay for Nociception: Mice were removed from their home cage and placed on a 55.0° C. (+/−0.2° C.) hot plate, and the latency to the first hind limb response was recorded. A Plexiglas enclosure was placed around the subject to keep them from walking off of the plate. The hind paw response is a foot shake, paw lick, or jump. The maximum time allowed for a hind limb response to occur was 30 seconds, after which the mouse was removed if a hind limb response had not occurred.

Open Field Assay for Anxiety Related Responses and Locomotor/Exploratory Activity: Anxiety-related, locomotor, and exploratory responses were measured in a clear Plexiglas (40 cm×40 cm×30 cm) open-field arena. A mouse was placed in the center of the arena and allowed to explore for 20 minutes. Overhead high-level lighting provides additional room lighting to enhance anxiety-related behaviors. Activity in the open field was quantified by a computer-controlled Versamax optical animal activity system (Accuscan Instruments, Columbus, Ohio) containing 16 photoreceptor beams on each side of the arena, thereby dividing the arena into 256 equally-sized squares. An additional set of photobeams was placed above this set to record vertical activity, and a set was placed below to record nose poke activity, thus giving three levels of recordable activity. Total distance traveled (locomotor activity), number of rearing and nose poke events (exploratory activity), and center distance (i.e., the distance traveled in the center of the arena) were recorded. The center distance was divided by the total distance traveled to obtain a center distance:total distance ratio. The center distance:total distance ratio can be used as an index of anxiety-related responses. Data was collected in four-minute intervals over the 20 minute test session.

Rotarod Assay for Motor Coordination: Motor coordination and balance were tested using an accelerating rotarod (Accuscan Instruments, Columbus, Ohio). The test was performed by placing a mouse on a rotating drum (measuring 3 cm in diameter) and recording the time each animal was able to stay on the rotating rod. Some mice hold on to the rotating rod as they begin to fall and ride completely around the rod. The speed of the rod accelerates from 0 to 40 rpm over the length of the 5 minute test. Mice were given four consecutive trials with a maximum time of 300 seconds (5 min).

Prepulse Inhibition of the Acoustic Startle Response: Prepulse inhibition of the acoustic startle response was measured using the SR-Lab System (San Diego Instruments, San Diego, Calif.). A test session began by placing a mouse in the Plexiglas cylinder where it was left undisturbed for 3 min. A test session consists of three trial types. One trial type was a 40 ms, 120 decibel (dB) sound burst alone that is termed the startle stimulus. There were four different acoustic prepulse plus startle stimulus trial types. The prepulse sound is presented 100 ms before the startle stimulus. The 20 ms prepulse sounds are at 74, 78, 82, and 90 dB. Finally, there were trials where no stimulus is presented to measure baseline movement in the cylinders. Six blocks of the six trial types were presented in pseudorandom order, such that each trial type was presented once within a block of seven trials. The average intertrial interval was 15 sec with a range of 10 to 20 seconds. The startle response is recorded for 65 ms (measuring the response every 1 ms) starting at the onset of the startle stimulus. The background noise level in each chamber is approximately 70 dB. The maximum startle amplitude recorded during the 65 ms sampling window (Vmax) was used.

The formula used to calculate % prepulse inhibition of a startle response is: 100-[(startle on acoustic prepulse+startle stimulus trials/startle response alone trials)×100.]

Sixteen (16) mice were analyzed; eight (8) homozygous (6 males, 2 females), four (4) heterozygous (2 males and 2 females), and four (4) wild-type (2 males and 2 females) mice. There were no notable differences in any of the parameters measured between the groups.

6.1.7 Radiology

One (1) male wild type (+/+) mouse and four (4) homozygous (−/−) mice (2 males and 2 females) were subject to examination using a mouse-size computer aided tomography (CT) scanning unit, the MicroCAT™ (ImTek, Inc., Knoxville, Tenn.). The mice were injected with a CT contrast agent, Omnipaque 300 (Nycomed Amersham, 300 mg of iodine per ml, 0.25 ml per animal, or 2.50–3.75 g iodine/kg body weight), intraperitoneally. After resting in the cage for approximately 10 minutes, the mice were sedated by intraperitoneal injection of Avertin (1.25% 2,2, 2,-tribromoethanol, 20 ml/kg body weight). The CT-scan was done with the anesthetized animal lying prone on the test bed. Three dimensional images were reconstructed by the Feldkamp algorithm in a cluster of workstations using ImTek 3D RECON software.

Significant depletion of fat depots in the abdominal and subcutaneous regions was noted for the 2 female (−/−) mice. There were no additional radiologic findings of significance that differentiated the mice of any genotypic group. The following observations were made for all groups of mice. There were no abnormalities observed in the skull, spine, tail or individual bones. The head, brain and neck appeared normal. The cervical lymph nodes were not enlarged. The lung fields were clear. The hearts were of normal size. The mediastinum and vessels revealed no abnormalities. The liver, spleen and kidneys were normal in size, shape and position. The rate of excretion of contrast media from the kidneys was within normal limits, indicating normal kidney function. The lymph nodes, and other abdominal organs, such as the adrenals, ovaries and prostate were normal. No lesions were observed in the soft tissues (skin, muscle or fat).

6.1.8 Blood Pressure and Heart Rate Determination

In an additional study, blood pressure was determined in eight (8) homozygous (6 males, 2 females) and four (4) wild-type (2 males and 2 females) mice. Mice were subjected to a conscious systolic blood pressure protocol similar to that previously described (Krege et al., 1995, Hypertension 25:1111–1115). Briefly, mice were placed on a heated platform (37° C.) with their tails placed through a cuff and in a sensor to detect the systolic blood pressure. The blood pressure was measured 20 times a day for 4 consecutive days—the first ten measurements are discarded to allow the animals to acclimate, and then the next ten measurements are recorded. There was no significant difference in the average systolic blood pressure between the wild-type mice and the homozygous mice.

Additionally, the heart rate was measured in eight (8) homozygous (6 males, 2 females) and four (4) wild-type (2 males and 2 females) mice. There was no significant difference in the heart rate between the wild-type mice and the homozygous mice.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. A recombinant expression vector comprising an isolated nucleic acid molecule that encodes the amino acid sequence shown in SEQ ID NO:2.

2. The recombinant expression vector of claim 1, wherein said isolated nucleic acid molecule comprises the nucleic acid sequence of SEQ ID NO:1.

3. A host cell comprising the recombinant expression vector of claim 1.

* * * * *